US012745956B2

(12) United States Patent
Helmer et al.

(10) Patent No.: US 12,745,956 B2
(45) Date of Patent: Sep. 29, 2026

(54) WEARABLE MEDICAL DEVICE

(71) Applicant: Sanofi, Paris (FR)

(72) Inventors: Michael Helmer, Frankfurt am Main (DE); Martin Vitt, Frankfurt am Main (DE)

(73) Assignee: Sanofi, Paris (FR)

( * ) Notice: Subject to any disclaimer, the term of this patent is extended or adjusted under 35 U.S.C. 154(b) by 397 days.

(21) Appl. No.: 18/034,857

(22) PCT Filed: Nov. 1, 2021

(86) PCT No.: PCT/EP2021/080238
§ 371 (c)(1),
(2) Date: May 1, 2023

(87) PCT Pub. No.: WO2022/096408
PCT Pub. Date: May 12, 2022

(65) Prior Publication Data
US 2024/0016450 A1 Jan. 18, 2024

(30) Foreign Application Priority Data
Nov. 4, 2020 (EP) .................................... 20315444

(51) Int. Cl.
*A61B 5/00* (2006.01)

(52) U.S. Cl.
CPC .......... *A61B 5/6802* (2013.01); *A61B 5/4839* (2013.01); *A61B 5/7405* (2013.01);
(Continued)

(58) Field of Classification Search
CPC ... A61B 5/7405; A61B 5/6802; A61B 5/4839; A61B 2562/0204; G16H 40/63
(Continued)

(56) References Cited

U.S. PATENT DOCUMENTS 10,024,667 B2 * 7/2018 Moore .................. G01C 21/20
11,611,705 B1 * 3/2023 Chen ...................... H04N 23/69
(Continued)

FOREIGN PATENT DOCUMENTS

CN 203724425 7/2014
CN 203724425 U * 7/2014
(Continued)

OTHER PUBLICATIONS

CN-203724425-U (machine translation) (Year: 2014).*
(Continued)

*Primary Examiner* — Yuqing Xiao
*Assistant Examiner* — Christopher Richard Walker
(74) *Attorney, Agent, or Firm* — Fish & Richardson P.C.

(57) ABSTRACT

A wearable medical device includes: a spatial sensor configured to determine distance to objects in an environment in front of the spatial sensor; an acoustic signal generator operable to generate an acoustic signal; a processor; and a memory configured to store instructions which, when executed the processor, cause the wearable medical device to: detect, using the spatial sensor, objects in the environment, calculate the distance to objects detected in the environment, and when the distance to an object is less than a predetermined value, control the acoustic signal generator to generate a first alert.

20 Claims, 11 Drawing Sheets

100

(52) U.S. Cl.
CPC ...... *A61B 5/746* (2013.01); *A61B 2562/0204* (2013.01); *A61B 2562/0233* (2013.01)

(58) Field of Classification Search
USPC ............................................................ 367/99
See application file for complete search history.

(56) References Cited

U.S. PATENT DOCUMENTS

| | | | | |
|---|---|---|---|---|
| 2009/0122161 | A1 | 5/2009 | Bolkhovitinov | |
| 2012/0053826 | A1* | 3/2012 | Slamka | G01C 21/20 701/301 |
| 2014/0085446 | A1* | 3/2014 | Hicks | G09B 21/001 348/62 |
| 2016/0091606 | A1* | 3/2016 | Shin | G01S 15/08 367/99 |
| 2016/0242988 | A1* | 8/2016 | Stevens | A61B 5/4806 |
| 2018/0228403 | A1 | 8/2018 | Li | |
| 2018/0242920 | A1* | 8/2018 | Hresko | A61B 5/0006 |

FOREIGN PATENT DOCUMENTS

| | | | | |
|---|---|---|---|---|
| CN | 107030714 | | 8/2017 | |
| CN | 109620660 | | 4/2019 | |
| CN | 107507457 | | 11/2019 | |
| CN | 110522617 | A | 12/2019 | |
| CN | 210056696 | | 2/2020 | |
| JP | S61-12112 | A | 1/1980 | |
| JP | S56-113996 | U | 9/1981 | |
| JP | S57-11516 | A | 1/1982 | |
| JP | H09-259366 | A | 10/1997 | |
| JP | 2017-218012 | A | 12/2017 | |
| KR | 10-2013-0115042 | | 10/2013 | |
| KR | 101463986 | B1 * | 12/2014 | A61F 9/08 |
| WO | WO 2019/240269 | A1 | 12/2019 | |
| WO | WO 2022/096408 | | 5/2022 | |

OTHER PUBLICATIONS

KR-101463986-B1 (Year: 2014).*

Sohn et al. ("Alarm system for elder patients medication with IoT-enabled pill bottle." 2015 International Conference on Information and Communication Technology Convergence (ICTC). IEEE, 2015.) (Year: 2015).*

Xiao et al. ("An assistive navigation framework for the visually impaired." IEEE transactions on human-machine systems 45.5 (2015): 635-640.) (Year: 2015).*

Bai et al. ("Smart guiding glasses for visually impaired people in indoor environment." IEEE Transactions on Consumer Electronics 63.3 (2017): 258-266.) (Year: 2017).*

International Search Report and Written Opinion in International Appln. No. PCT/EP2021/080238, mailed on Jan. 21, 2022, 10 pages.

International Preliminary Report on Patentability in International Appln. No. PCT/EP2021/080238, mailed on May 19, 2023, 8 pages.

* cited by examiner

WEARABLE MEDICAL DEVICE

CROSS-REFERENCE TO RELATED APPLICATIONS

The present application is the national stage entry of International Patent Application No. PCT/EP2021/080238, filed on Nov. 1, 2021, and claims priority to Application No. EP 20315444.8, filed on Nov. 4, 2020, the disclosures of which are incorporated herein by reference.

TECHNICAL FIELD

The present disclosure relates to a wearable medical device and in particular, to a wearable medical device that acts as an aid to those with a visual impairment.

BACKGROUND

A variety of medical conditions exist which can impair a patient's eyesight. Visual impairments can be directly associated with the function of a patient's eyes, in that the patient may be partially or completely blind. Alternatively, visual impairments can occur indirectly as a secondary effect of other medical conditions, such as those affecting joints, muscle or tissue. These can cause changes to patient posture, which can restrict the patient's field of view. For instance, patients with rheumatism or, more specifically, ankylosing spondylitis may have a restricted range of movement in their neck or back, such that they are unable to stand upright to look ahead or turn their head within a normal range.

These medical conditions can impair eyesight in such a way that it is difficult for patients to determine their surroundings, move between locations and complete tasks. In particular, for those patients who require regular treatment, for instance by injection of a medicament by a medical device, visual impairment can make locating the correct medical device, handling the medical device or identifying a suitable injection site more difficult.

SUMMARY

Aspects of this disclosure relate to a device that can assist patients to navigate their surrounding environment and administer medicaments safely and reliably on a daily basis.

In accordance with an aspect of the present disclosure, there is provided a wearable medical device comprising a spatial sensor configured to determine distance to objects in an environment in front of the spatial sensor, an acoustic signal generator operable to generate an acoustic signal, a processor; and a memory. The memory is configured to store instructions which, when executed the processor, cause the wearable medical device to detect, using the spatial sensor, objects in the environment, calculate the distance to objects detected in the environment, and when the distance to an object is less than a predetermined value, control the acoustic signal generator to generate a first alert.

The provision of an alert in response to the proximity of objects detected by the device provides a system of feedback to the user that indicates the presence of objects in the surrounding environment with respect to the user. This configuration minimises the likelihood that a user will unintentionally contact an object and cause injury to themselves or damage to the object.

The instructions when executed by the processor may further cause the wearable medical device to: when the distance to an object is greater than a predetermined value, control the acoustic signal generator to generate a second alert. The second alert may be different to the first alert.

This provision of first and second alerts provides a system of feedback to the user that indicates the presence and spatial distribution of objects in the surrounding environment with respect to the user. In this way, the spatial sensor allows a dynamic output of alerts to be provided to the user, as the user moves through an environment.

The acoustic signal generator may comprise a pair of acoustic signal generators, one of the pair provided on each side of the device and the instructions when executed by the processor, may further cause the wearable medical device to: when the distance to an object is greater than a predetermined value, control the pair of acoustic signal generators to generate an alert alternately on each side of the device.

The provision of alternating alerts provides a system of feedback to the user that enables the user to effectively move safely through an environment. In other words, so that the user does not unintentionally contact objects in that environment.

The wearable medical device may further comprise an acoustic sensor configured to detect environmental acoustic signals and the instructions when executed by the processor, may further cause the wearable medical device to: control the acoustic sensor to detect environmental acoustic signals, and control the acoustic signal generator to generate alerts having acoustic properties that are selected based on the environmental acoustic signals detected.

The use of an acoustic sensor is beneficial as enables the alert generated to be customised to the surrounding environmental conditions in a way that improves the likelihood that the alert will be recognised and understood or acknowledged.

The wearable medical device may further comprise an optical sensor configured to capture images of the environment and the instructions when executed the processor, may further cause the wearable medical device to: capture, using the optical sensor, at least one image of the environment, identify, in the at least one image, objects in the environment, verify distances of objects in the environment based on a comparison with objects detected in the environment using the spatial sensor.

This configuration is advantageous as it improves the accuracy and reliability by which the presence and distance to objects in the environment are detected. This improves the reliability of the device as a means of safely guiding a user through an environment.

The wearable medical device may further comprise a light source and the instructions when executed by the processor, may further cause the wearable medical device to: when the distance to an object is greater than a predetermined value, control the light source to flash at a first speed, and when the distance to an object is less than a predetermined value, control the light source to flash at a second speed.

The use of a light source is beneficial as it can be detected in the peripheral vision of the user without being overly intrusive. The alert provided by the light source provides an additional means of feedback to the user that indicates the presence and spatial distribution of objects in the surrounding environment with respect to the user. The provision of a visual indicator can improve the likelihood that the alert will be recognised and understood.

The wearable medical device may further comprise a light source, and the instructions when executed by the processor, may further cause the wearable medical device to: when the acoustic sensor detects environmental acoustic signals above a first predetermined value or below a second predetermined value, control the light source to flash and the acoustic signal generator not to generate an acoustic signal, and when the acoustic sensor detects environmental acoustic signals in a range between the first predetermined value and the second predetermined value, control the light source to flash and the acoustic signal generator to generate an alert.

This configuration is advantageous as it provides a system that distinguishes between the spatial distribution of objects in the environment (e.g. their relative distance to the user). This improves the functionality of the device as a means of safely guiding a user through an environment.

The light source may further comprise a pair of light sources, one of the pair provided on each side of the device, and the instructions when executed by the processor, may further cause the wearable medical device to: control the light source on a left side to flash when an object is identified in the environment to the left of the wearable medical device and the distance to the object is less than a predetermined value, control the light source on a right side to flash when an object is identified in the environment to the right of the wearable medical device and the distance to the object is less than a predetermined value, control the light source on the left side and the light source on the right side to flash when an object is identified in the environment in front of the wearable medical device and the distance to the object is less than a predetermined value.

The instructions when executed by the processor, may further cause the wearable medical device to control the light source on the left side and the light source on the right side to flash alternately when the distance to an object is greater than a predetermined value.

The instructions when executed by the processor may further cause the wearable medical device to: control the acoustic signal generator on a left side to generate an alert when an object is identified in the environment to the left of the wearable medical device and the distance to the object is less than a predetermined value, control the acoustic signal generator on a right side to generate an alert when an object is identified in the environment to the right of the wearable medical device and the distance to the object is less than a predetermined value, and control the acoustic signal generator on the left side and the acoustic signal generator on the right side to generate an alert when an object is identified in the environment in front of the wearable medical device and the distance to the object is less than a predetermined value.

The provision of multiple sensors on different sides of the housing extends the area of the surrounding environment that is monitored.

The provision of alternating alerts in response to the spatial distribution of objects in the surrounding environment provides a system of feedback to the user that enables the user to differentiate between objects based on distance and thereby move more efficiently through an environment.

The wearable medical device may further comprise a housing that is pivotally mounted to a side of the device, the housing comprising at least one sensor and an actuator configured to pivot the housing with respect to device, and the instructions when executed by the processor, further cause the wearable medical device to: control the actuator to adjust an orientation of the housing to an angle that is horizontal with respect to a body posture of a user.

This arrangement is advantageous as it enables the field of view of the device to be adapted, thereby improving the operability of the device.

The housing may comprise a pair of housings, one located on each side of the wearable medical device, and one housing may include a first optical sensor and the other housing includes a second optical sensor, and the instructions when executed by the processor, may further cause the wearable medical device to: control the first optical sensor to capture at least one image of the environment from a first position on one side of the device, control, at the same time, the second optical sensor to capture at least one image of the environment from a second position on the other side of the device, and process the two images to generate a stereoscopic image.

The provision of multiple sensors on different sides of the housing extends the area of the surrounding environment that is monitored. This is advantageous as it improves the accuracy and reliability by which the presence of objects and distance to objects in the environment are detected. The provision of a stereoscopic image can improve the likelihood that an object will be recognised and acknowledged. This improves the reliability of the device as a means of identifying objects and thereby orientating a user with respect to an environment.

The memory may be further configured to store at least one predefined set of distinctive features associated with a drug delivery device, and the instructions when executed by the processor, may further cause the wearable medical device to: capture at least one image of a drug delivery device; identify, in the at least one image, at least one distinctive feature of the drug delivery device; compare the at least one distinctive feature identified to the at least one predefined set of distinctive features; when the drug delivery device is identified, based on a match of the at least one distinctive feature with at least one distinctive feature of the predefined set of distinctive features, control the acoustic signal generator to generate a third alert; and when the drug delivery device is not identified, based on no match of the at least one distinctive feature with at least one distinctive feature of the predefined set of distinctive features, control the acoustic signal generator to generate a fourth alert. The third alert may be different to the fourth alert.

The provision of additional different alerts provides a system of feedback to the user as to whether the correct drug delivery device has been selected. In other words, whether the user is handling the correct drug delivery device intended for use by the user. This is advantageous as reduces the likelihood of incorrect drug management.

The at least one predefined set of distinctive features may identify a status of the drug delivery device, including one or more of: a type of drug delivery device, a medicament loaded in the drug delivery device, a dose dialed at the drug delivery device, an ejection of a dose from the drug delivery device.

This improves the safety of handling and managing drug delivery devices.

The wearable medical device may further comprise a wireless unit configured to connect to a wireless network, and the memory may be further configured to store a home assistant application, and when the wireless unit is connected to a wireless network in a home environment, the home assistant application is executed by the processor and causes the wearable medical device to: capture, using the optical sensor, at least one image in the home environment, identify in the at least one image objects in the home environment, determine, using the spatial sensor, distances between objects identified in the home environment, based on the at least one image, the distances between objects, and WiFi positioning generate a floor plan representing the home environment including the objects, and store the floor plan in the memory.

This configuration is advantageous as it provides a system of mapping a local or known environment to enable the user to move more efficiently through the environment.

The device may a pair of glasses. This is particularly beneficial as a means of identifying objects in an environment for those with visual impairments. The glasses may function as an electronic white stick.

The wearable medical device may further two or more acoustic signal generators on each side of the device.

The optical sensor may further comprise two or more cameras provided on each side of the device.

The provision of multiple sensors on different sides of the housing extends the area of the surrounding environment that is monitored, thereby improving the accuracy and reliability by which objects in the environment are detected and the likelihood that a user recognises and understands an alert.

In accordance with a second aspect of the present disclosure, there is provided a method of using a wearable medical device. The wearable medical device comprises a spatial sensor, a processor, and a memory, and the method comprises: detecting, using the spatial sensor, objects in the environment, calculating the distance to objects detected in the environment, when the distance to an object is less than a predetermined value, controlling the acoustic signal generator to generate a first alert.

The method may further comprise: when the distance to an object is greater than a predetermined value, controlling the acoustic signal generator to generate a second alert. The second alert may be different to the first alert.

The wearable medical device may further comprise an optical sensor, and the method may further comprise: storing, in the memory, at least one predefined set of distinctive features associated with a drug delivery device, capturing, using the optical sensor, at least one image of a drug delivery device; identifying, in the at least one image, at least one distinctive feature of the drug delivery device, comparing the at least one distinctive feature identified to the at least one predefined set of distinctive features, when the drug delivery device is identified, based on a match of the at least one distinctive feature with at least one distinctive feature of the predefined set of distinctive features, controlling the acoustic signal generator to generate a third alert; and when the drug delivery device is not identified, based on no match of the at least one distinctive feature with at least one distinctive feature of the predefined set of distinctive features, controlling the acoustic signal generator to generate a fourth alert. The third alert may be different to the fourth alert.

The wearable medical device may further comprise a wireless unit, and the method may further comprise: establishing a connection to a wireless network in a home environment; detecting, using the spatial sensor, objects in the home environment; calculating, using the spatial sensor, distances between objects detected in the home environment; capturing, using the optical sensor, images of the home environment; identifying objects in the images of the home environment; verifying objects in the environment based on a comparison between objects in the images, objects detected using the spatial sensor and WiFi positioning; generating a floor plan representing the home environment including the objects; and storing, in the memory, the floor plan.

The wearable medical device may further comprise an acoustic signal generator, and the method may further comprise: capturing an image of a drug delivery device in the home environment; comparing the image of the home environment to the floor plan; recognising a location of the drug delivery device in the home environment based on the floor plan; storing a record of the location of the drug delivery device in the home environment; and in response to a user input, controlling the acoustic signal generator to output an alert when the user is proximal to the location of the drug delivery device based on the record.

In accordance with a third aspect of the present disclosure, there is provided a computer program comprising machine readable instructions that when executed by a processing arrangement, cause the processing arrangement to perform the method of using a wearable medical device according to the second aspect of the disclosure.

Embodiments of the present disclosure will now be described, by way of example only, with reference to the accompanying drawings.

DETAILED DESCRIPTION

Figure 1:
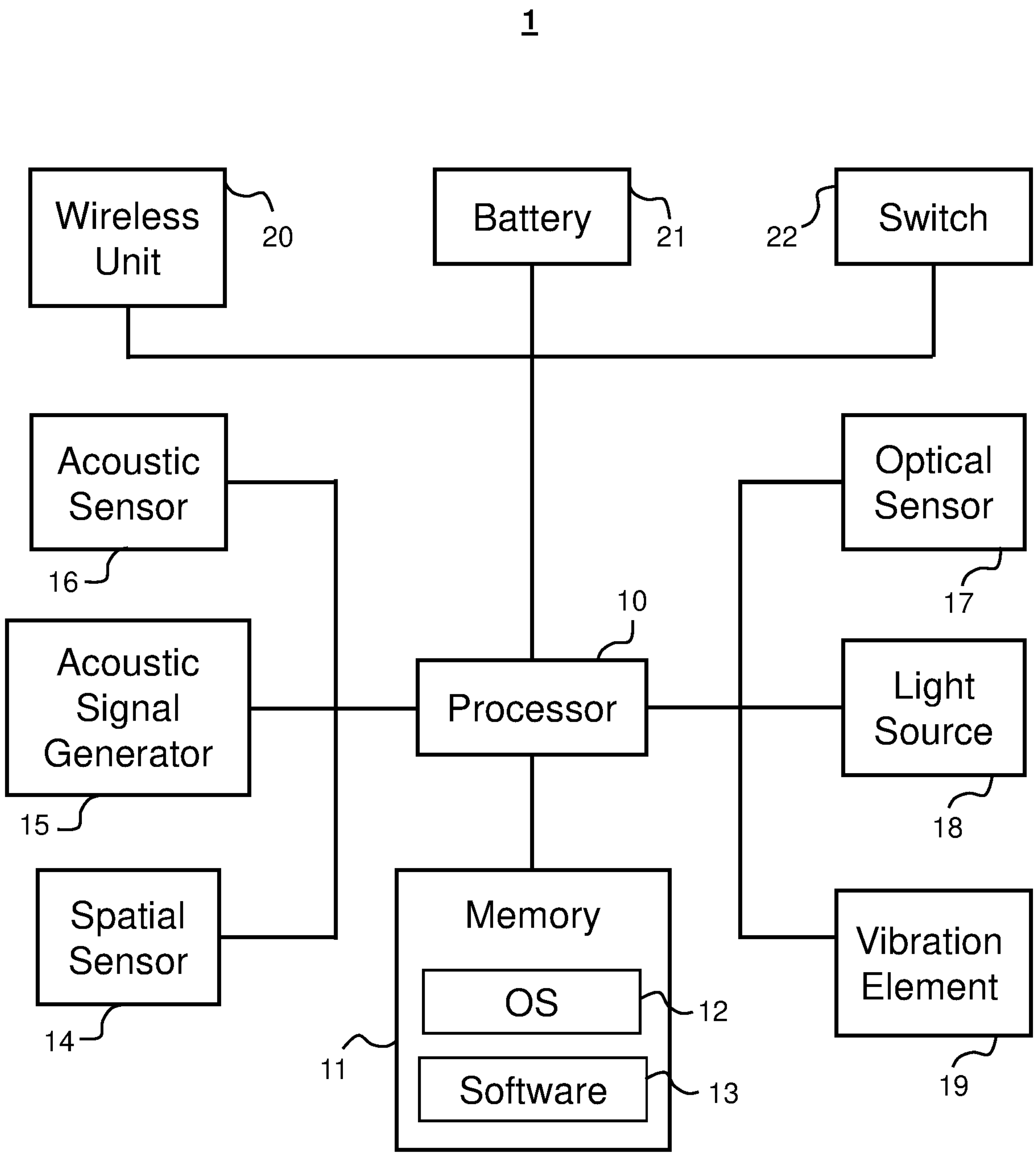
FIG. 1 is a block diagram of components of a wearable medical device 1 according to embodiments of the present disclosure.

FIG. 1 is a block diagram showing components of a wearable medical device 1 according to embodiments of the present disclosure. The components include a controller or processor 10. The processor 10 controls operation of the other hardware components of the device 1. The processor 10 and other hardware components may be connected via a system bus (not shown). Each hardware component may be connected to the system bus either directly or via an interface.

The wearable medical device 1 comprises a memory 11, i.e. a working or volatile memory, such as Random Access Memory (RAM), and a non-volatile memory. The volatile memory may be a RAM of any type, for example Static RAM (SRAM), Dynamic RAM (DRAM) or a Flash memory. The processor 10 may access RAM in order to process data and may control the storage of data in the memory 11. The non-volatile memory may be of any kind, such as a Read Only Memory (ROM), a flash memory and a magnetic drive memory. The non-volatile memory stores an operating system (OS) 12 and one or more software modules 13, as well as storing data files and associated metadata. The software modules 13 represent instructions for operating the device. These instructions may be distinct, discrete applications that may be provided in the wearable medical device 1 on manufacture or downloaded into the device 1 by a user, for instance from an application market place or application store.

The processor 10 is configured to send and receive signals to and from the other components in order to control operation of the other components. The processor 10 operates under control of the operating system 12. The operating system 12 may comprise code relating to hardware, as well as the basic operation of the wearable medical device 1. The operating system 12 may also cause activation of one or more other software modules 13 stored in the memory 11.

The wearable medical device 1 includes a spatial sensor 14. The spatial sensor 14 detects objects in an environment surrounding the device. In doing so, the spatial sensor 14 determines the distance to the objects detected in the environment. In other words, the spatial sensor 14 determines or calculates the distance between the wearable medical device 1 and objects. The spatial sensor 14 outputs a signal representing the determined distance. The spatial sensor 14 may be any suitable type of spatial sensor 14 capable of determining the distance to objects detected in the surrounding environment. For instance, the spatial sensor 14 may be a laser distance sensor (e.g. LiDAR), a photoelectric distance sensor or an ultrasonic sensor (e.g. an ultrasonic time-of-flight range sensor).

The spatial sensor 14 or the processor 10 may equally well be responsible for processing and analysing (calculating) the distance to detected objects. For instance, the distances calculated may be compared to a predetermined distance value. The predetermined distance value is stored in the memory 11 and may be provided on manufacture or it may be set by a user. For instance, the predetermined distance value may be provided as a default value on manufacture that can be subsequently adjusted by the user. The predetermined value represents a safe distance between the user and objects detected in the environment. The predetermined distance value is intended to prevent the user making unintentional contact with objects in the surrounding environment. In other words to prevent the user from hitting, tripping over or knocking over objects in the surrounding environment.

The wearable medical device 1 includes an acoustic signal generator 15. The processor 10 controls the acoustic signal generator 15. The acoustic signal generator 15 may be any suitable type of electric acoustic signal generator 15 capable of emitting a synthesised audio signal. For instance, the acoustic signal generator 15 may be a speaker.

The processor 10 controls the acoustic signal generator 15 to generate (output) an alert. The alert is an audible alert that provides an acoustic feedback for the user. The alert may be emitted continuously or intermittently. The alert may be any suitable form of alert, for instance, a beep, a chirp, a click or a piece of music. The alert may be a pre-recorded sound. Alternatively, the alert may be synthesised by the acoustic signal generator 15 under control of the processor 10. The pre-recorded sound may be stored in the memory 11 of the wearable medical device 1.

The wearable medical device 1 may also include an acoustic sensor 16. The processor 10 controls the acoustic sensor 16. The acoustic sensor 16 is configured to detect environmental acoustic signals. The acoustic sensor 16 is thereby able to detect the surrounding environmental conditions as characterised by the acoustic signals emitted in that environment.

The environmental conditions may indicate that the user is in a quiet environment or a loud environment, for instance. The acoustic sensor 16 may be any suitable type of acoustic sensor 16 capable of detecting environmental acoustic signals. For instance, the acoustic sensor 16 may be a microphone, such as a moving coil or dynamic microphone, a condenser microphone or a piezoelectric microphone.

The acoustic sensor 16 or the processor 10 may equally well be responsible for processing and analysing the detected acoustic signals. For instance, the detected acoustic signals may be compared to a predetermined acoustic signal value. The predetermined acoustic signal value is stored in the memory 11 and may be provided on manufacture or it may be set by the user. For instance, the predetermined acoustic signal value may be provided as default value on manufacture that can be subsequently adjusted by the user. The predetermined acoustic signal value includes a maximum value (or first value) and/or a minimum value (or second value). The maximum value is indicative of loud environments, where the use of an acoustic feedback signal would be unlikely to be heard by the user. The minimum value is indicative of quiet environments, where it would be undesirable to emit an acoustic alert. Thus, acoustic signals detected in the range between the first predetermined value and the second predetermined value are regarded as within a normal range (e.g. conditions indicative of general ambient environmental noise). Within a normal range the emission of an acoustic feedback signal would be appropriate.

The wearable medical device 1 may also include an optical sensor 17. The processor 10 controls the optical sensor 17. The optical sensor 17 is capable of capturing one or more images of the environment surrounding the device. This may include one or more still images or a video. The optical sensor 17 may be a camera of any suitable type. The optical sensor 17 or the processor 10 may equally well be responsible for processing and analysing the captured images.

As described above, the wearable medical device 1 includes a spatial sensor 14 and may additionally include an optical sensor 17, each of which are capable of determining information from the environment surrounding the device. With respect to these sensors, the surrounding environment encompasses the area within a field-of-view of the sensor. The field-of-view of the sensor extends forward of the sensor. The field-of-view of each sensor will be dictated by the direction in which wearable medical device 1 is orientated and/or the location of the sensor housed in the device. If a sensor is located on the front of the device, the field-of-view will encompass the area in front of, or generally forward of, the device. Alternatively, if an a sensor is located on the side of the device, the field-of-view will encompass the area in front of the side of the device, and so on. The field-of-view includes at least a 90 degree area forward of the sensor. The field-of-view may also encompasses a 180 degree area forward of the sensor. However, the field-of-view may not be limited to an 180 degree area and it may be possible to encompass a larger area, such as a 270 degree area, according to the capability of the sensor used.

The wearable medical device 1 may also include a light source 18. The processor 10 controls the light source 18. The light source 18 may be any suitable kind, such as a light emitting diode 18. The light source 18 is capable of emitting light in a number of ways. For instance, the light source 18 may be turned on to emit a continuous source of light, the light source 18 may flash (i.e. is turned on/off intermittently), and/or the light source 18 may change colour. The light source 18 may also flash according to different speeds or different patterns (e.g. a 'dot-dash' type pattern). The provision of a light source 18 is not essential, for instance, where the wearable medical device 1 is intended for use by a blind user.

The wearable medical device 1 may also include a vibration element 19, although this is not essential. The processor 10 also controls the vibration element 19. The vibration element 19 is any suitable kind capable of emitting a tactile or haptic feedback. For instance, the vibration element 19 may be a mechanical or an electronic device (e.g. piezoelectric or moving coil).

The vibration element 19 may work in combination with the acoustic signal generator 15 to provide a tactile alert (e.g. a silent vibration) at substantially the same time as an audible alert. Alternatively, a tactile alert may be generated via the vibration element 19 instead of an audible alert. This may be implemented, for instance, when the wearable medical device 1 is configured to operate in a private mode or silent mode. Alternatively, the vibration element 19 may provide a structure-borne sound in addition to a tactile feedback. The vibration element 19 may work in combination with the acoustic signal generator 15 to provide a structure-borne sound, in addition to the acoustic signal generated by the acoustic signal generator 15. The vibration element 19 may, for instance, provide an additional buzzing sound, as an acoustical feedback.

The wearable medical device 1 may also include a communication interface or unit and in particular, a wireless communication unit 20. The processor 10 controls the wireless unit 20. The wireless unit 20 is capable of establishing a wireless connection with an external device. The wireless unit 20 is capable of transmitting and/or receiving information to/from another device in a wireless fashion. Transmission may be based on radio transmission or optical transmission. The wireless unit 20 may be a Bluetooth transceiver or WiFi transceiver, for instance.

The wearable medical device 1 also houses a battery 21 to power the wearable medical device 1. The wearable medical device 1 may also include a switch 22, although this is not essential. The switch 22 may be of any suitable kind, for instance, a mechanical switch 22 (e.g. a slider, a rocker or a push button switch 22) or an electronic switch 22 (e.g. a touch sensor). The switch 22 functions to turn on/off the wearable medical device 1, in that if the processor 10 detects that the switch 22 is turned on/off the processor 10 turns the device on/off. Additionally or alternatively, the switch 22 may function to turn on/off a silent mode of the device 1, in that if the processor 10 detects that the silent mode is turned on/off, the processor 10 turns the acoustic signal generator 15 on/off.

In the following, embodiments of the present disclosure will be described with reference to a wearable medical device 1 implemented as a pair of glasses. The present disclosure is not, however, limited to such an application and the wearable medical device 1 may equally well be implemented in an alternative device, such as a mobile device (e.g. a smartphone).

Figure 2:
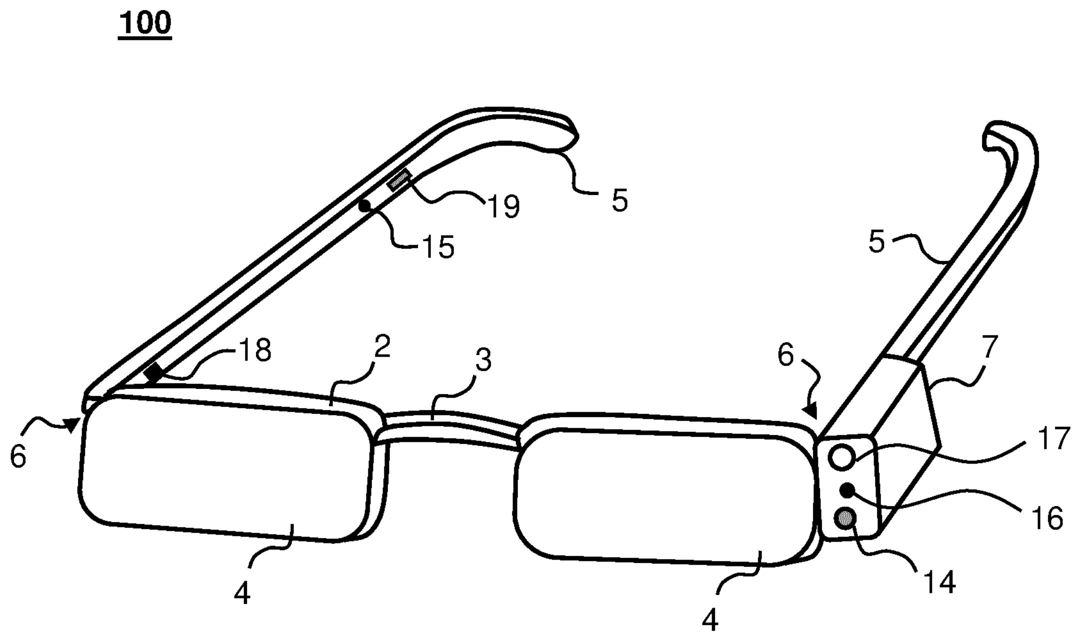
FIG. 2 is a perspective view of a wearable medical device 1 according to a first group of embodiments.

FIG. 2 shows a perspective view of the wearable medical device 1 according to a first group of embodiments in which the wearable medical device 1 is implemented as a pair of glasses 100.

In FIG. 2, the glasses 100 comprise a frame 2 including a bridge 3, a pair of lenses 4 and a pair of arms 5. Each arm 5 is coupled to the frame 2 by a hinge 6, to enable the arms 5 to rotate between a closed position and an open position. The arms 5 are in a closed position when they are folded against the frame 2 and in an open position when they extend perpendicular to the frame 2 (i.e. they are not folded). The pair of arms 5 may also be referred to as a left arm 5 and a right arm 5. Other standard or optional components of the glasses 100, such as nose pads, are omitted from description.

A housing 7 containing one or more electrical components is mounted to the glasses 100. In FIG. 2, the housing 7 is mounted to an arm 5 and/or the frame 2, and may be located proximal to the hinge 6. The housing 7 is mounted to an outer surface of an arm 5 and/or the frame 2. Alternatively, the housing 7 is integrally formed with the arm 5 and/or the frame 2. For instance, the housing 7 forms an integral part of an arm 5.

The housing 7 accommodates any one or any combination of the electrical components shown in FIG. 1. The housing 7 contains the processor 10, the spatial sensor 14, the acoustic signal generator 15, the memory 11 and the battery 21. The housing 7 may also contain any one or any combination of the acoustic sensor 16, the optical sensor 17, the light source 18, the vibration element 19 and the wireless unit 20. The housing 7 may further include a switch 22.

FIG. 2 shows an arrangement in which the spatial sensor 14, the acoustic sensor 16 and the optical sensor 17 are provided at the front of the housing 7 to face forward of the frame 2 of the glasses 100. In FIG. 2, the optical sensor 17, acoustic sensor 16 and spatial sensor 14 are vertically arranged of stacked with respect to each other. In other words, these sensors are aligned vertically, in that order, from top to bottom in the housing 7. However, the present disclosure is not limited to this and other arrangements may equally well be provided.

In FIG. 2, the acoustic signal generator 15 is provided on an arm 5 of the glasses 100. The acoustic signal generator 15 is provided on an inner surface of the arm 5, and may be located at a position that is proximal to the user's ear when the glasses 100 are worn.

The light source 18 is provided on an arm 5 of the glasses 100. The light source 18 is provided on an inner surface of the arm 5 and may be located at a position that is proximal to the user's eye when the glasses 100 are worn. For instance, the light source 18 is located adjacent to the hinge 6 of the glasses 100. Alternatively, if the housing 7 is integrally formed with the glasses 100, then the light source 18 may be provided on an inner surface of the housing 7, and preferably located adjacent to the hinge 6 of the glasses 100. The light source 18 may also be orientated at different angles with respect to the glasses 100 as appropriate, in order to maximise the likelihood that the user will recognise the operation of the light source 18. The light source 18 is intended as a visual indicator or visual feedback signal.

The vibration element 19 is also provided on an arm 5, although this is not essential. The vibration element 19 is positioned on an inner surface of the arm 5, and may be located at a position that is proximal to the user's ear when the glasses 100 are being worn. For instance, the vibration element 19 is located adjacent to the acoustic signal generator 15.

In the above description, a single acoustic signal generator 15, light source 18 and vibration element 19 is described as provided on an arm 5 of the glasses 100. However, the present disclosure is not limited to such an arrangement and more than one or any combination of these sensor may equally well be provided on one arm 5 or both arms 5 of the pair of arms 5.

Figure 3:
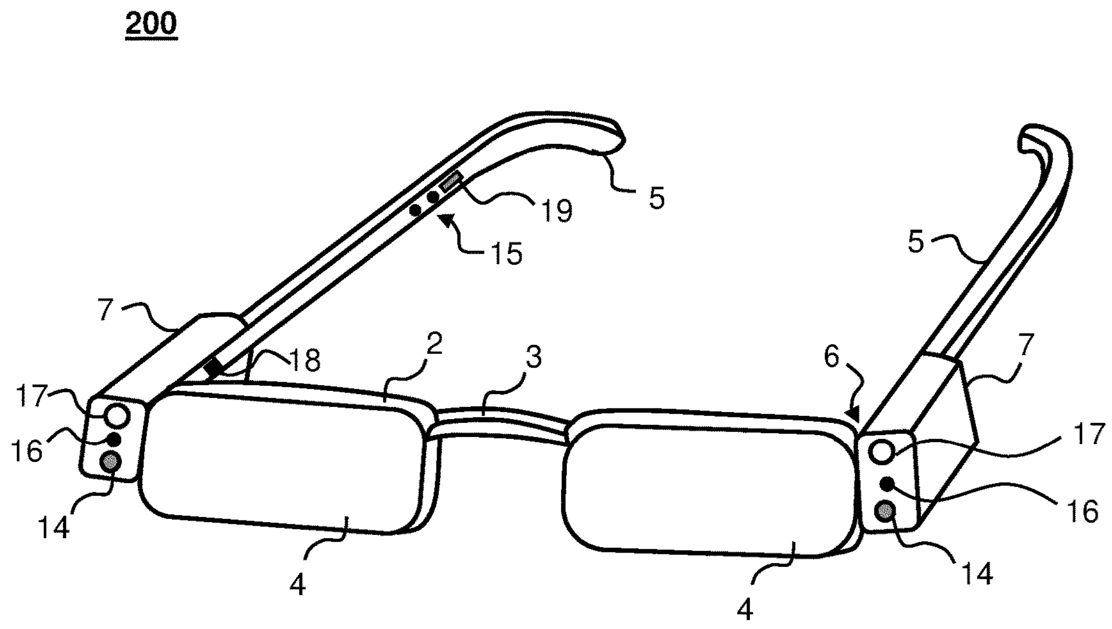
FIG. 3 is a perspective view of a wearable medical device 1 according to a second group of embodiments.
Figure 4:
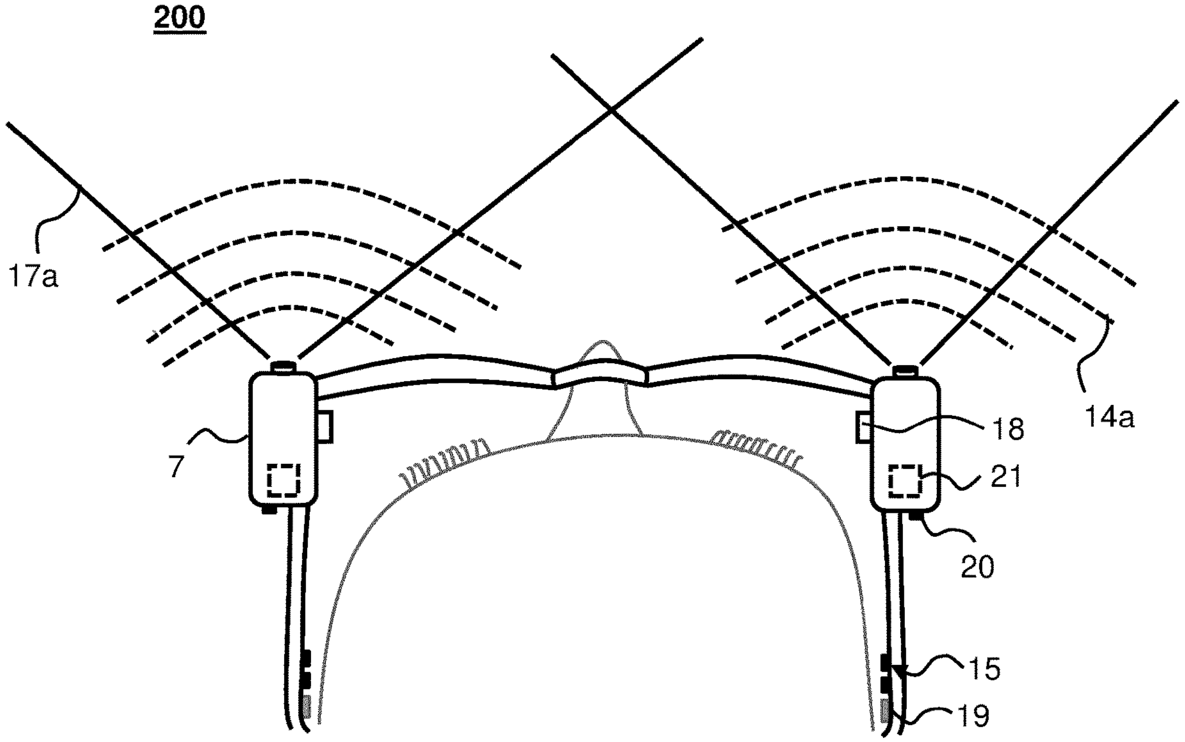
FIG. 4 is a plan view a wearable medical device 1 being worn by a user in accordance with a second group of embodiments.

FIGS. 3 and 4 show the arrangement of electronic components of the wearable medical device 1 as integrated with glasses 200 according to a second group of embodiments. FIG. 3 shows a perspective view of the pair of glasses 200 having a pair of housings 7 provided on either side of the frame 2. The glasses 200 and each housing 7 has substantially the same configuration as that described above with respect to the first group of embodiments shown in FIG. 2, such that a detailed description will be omitted.

The glasses 200 according to the second group of embodiments may include two or more acoustic signal generators on each side of the device. FIGS. 3 and 4 show that a pair of acoustic signal generators 15 is provided on each arm 5. Each pair of acoustic signal generators 15 is located on an inner surface of the arm 5, and may be located adjacent to each other at a position that is proximal to the user's ear when the glasses 200 are worn. The glasses 200 also include a pair of light sources 18. One of the pair of light sources 18 is located on each housing 7, as described above with respect to FIG. 2. The glasses 200 also include a pair of vibration elements 19. One of the pair of vibration elements 19 is located on the inner surface of each arm 5, as described above with respect to FIG. 2.

FIG. 4 shows schematic lines indicating examples of the general field-of-view 14*a* of the spatial sensor 14 and the field-of-view 17*a* of the optical sensor 17 based on the arrangement shown in FIG. 3. The optical sensor may include one camera on either side of the device or two or more cameras provided on each side of the device. The field-of-view is not limited to the distance or angle area shown by the lines, these are merely schematic to demonstrate the general concept that the sensors are capable of determining information from the environment surrounding the device.

FIG. 4 additionally shows a switch 22 provided on the housing 7. In particular, the switch 22 is located on the rear surface of the housing 7, although the present disclosure is not limited to this arrangement. The switch 22 may be provided in any suitable location that minimises interference with the user's head when the glasses 200 are worn.

FIG. 4 shows a dashed square indicating the location of the battery 21 in the housing 7. However, the present disclosure is not limited to this and the battery 21 may be provided in any suitable location of the housing 7 to supply power to the electronic components. The wireless unit 20 (not shown) is also accommodated within the housing 7.

FIG. 4 also shows that the switch 22, the battery 21 and the wireless unit 20 (not shown) are provided at or accommodated in each housing 7, but this is not essential. One or any combination of the switch 22, the battery 21 and the wireless unit 20 may equally well be provided in one or both housings 7.

According to the second group of embodiments, two or more acoustic signal generators may be provided on each side of the device. Similarly, the optical sensor may include two or more cameras provided on each side of the device.

Figure 5:
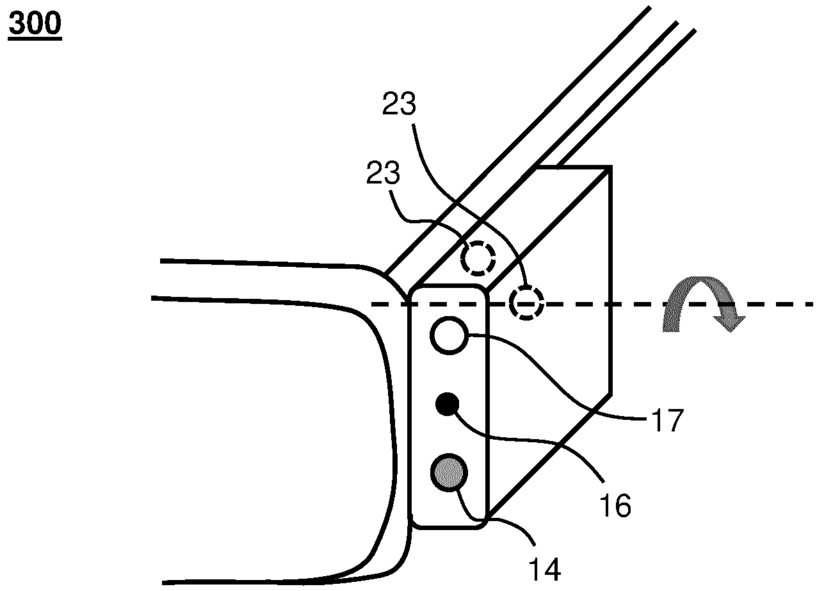
FIG. 5 is a perspective view of a portion of a wearable medical device 1 according to a third group of embodiments.
Figure 6:
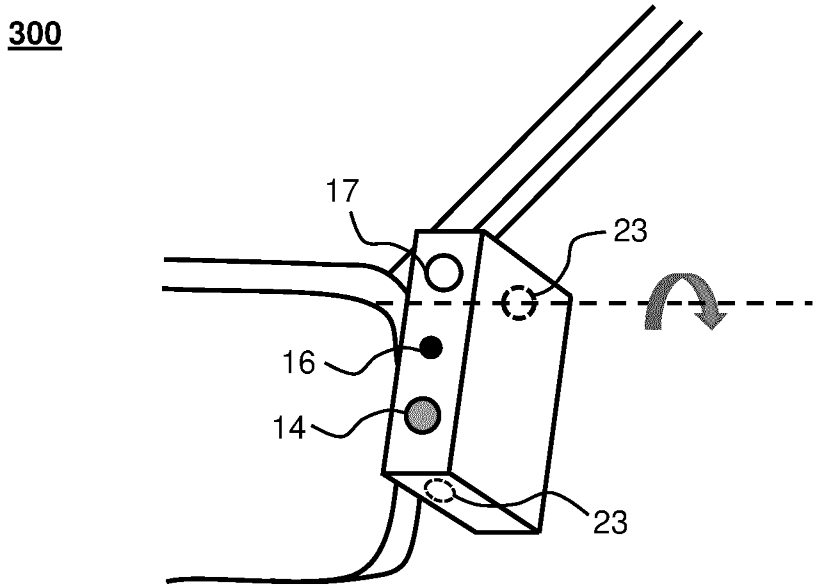
FIG. 6 is a perspective view of a portion of a wearable medical device 1 according to a third group of embodiments in which the housing 7 is tilted.

FIGS. 5 and 6 show glasses 300 according to a third group of embodiments. Here, one or more additional sensors 23 are located on other surfaces or sides of one or both of the housings 7 according to the first or second group of embodiments.

FIG. 5 shows an example in which additional sensors are located on the top side and the outer side of the housing 7. Another additional sensor may also be provided on the base of the housing 7. The additional sensors face forward of each respective side of the housing 7 at which they are located. The additional sensors may comprise one or any combination of a spatial sensor 14, an acoustic signal generator 15, an acoustic sensor 16, an optical sensor 17, a light source 18 or a vibration element 19. In one example, the additional sensors include spatial sensors 14 and optical sensors 17. The provision of multiple sensors on different sides of the housing 7 extends the area of the surrounding environment that is monitored.

FIGS. 5 and 6 also show embodiments in which the housing 7 is pivotally mounted to the glasses 300. The housing 7 includes a pivot mechanism that enables the housing 7 to couple to and pivot with respect to the glasses 300. The housing 7 is arranged to pivot about an axis parallel to the frame 2 or lenses 4 of the glasses 300 (that is the long axis of the frame 2), as indicated by the dashed line in FIGS. 5 and 6. The pivot mechanism can be implemented in one or both of the housings 7, where two housings 7 are provided. The pivot mechanism may be manually actuated by manipulating the housing 7 to the required angle by hand. Alternatively, the mechanism may be actuated by a motor (not shown) under the control of the processor 10. The pivot mechanism enables the housing 7 to rotate 180 degrees with respect to the glasses 300. However, the present disclosure is not limited to this and the housing 7 may pivot a full 360 degrees with respect to the glasses 300, or anywhere between greater than 0 and 360 degrees.

The pivot mechanism enables the angle of the housing 7 to be adapted to horizontal when the glasses 300 are worn by the user. In particular, the angle of the housing 7 may be adjusted based on the posture of the user wearing the glasses 300. This may be necessary where the user suffers from a medical condition that causes curvature of the spine or otherwise results in a restricted range of movement in the back or neck. Such medical conditions may prevent the user from standing upright and/or looking ahead or turning their head within a normal range. The pivot mechanism thereby enables the glasses 300 to monitor the surrounding environment in front of the user, even when the user is unable to look directly ahead or to the side. In addition, where the user is less able or unable to turn their head, the provision of multiple sensors on different sides of the housing 7 extends the area of the surrounding environment that is monitored.

Use of the wearable medical device 1 will now be described. In particular, use of the wearable medical device 1 when implemented as a pair of glasses is described. In use, the glasses are worn by a user. In brief, the wearable medical device 1 is configured to provide an alert in the form of an acoustic feedback that indicates to the user the presence of an object in the surrounding environment. In particular, the alert is based on the distance to the object in the surrounding environment. The alert may be adapted according to the detected environmental acoustic signals. The alert may be further adapted based on the location of the object. The alert may additionally or alternatively take the form of a visual and/or haptic feedback. The operations disclosed provide a means to guide a user through an environment without causing harm to the user by unintended contact with an object. Accordingly, the wearable medical device 1 can assume the function of an electronic white stick. These operations also aid in the handling of objects as the user is able to determine their proximity to said objects and whether the correct device is being handled and operated correctly.

Figure 7:
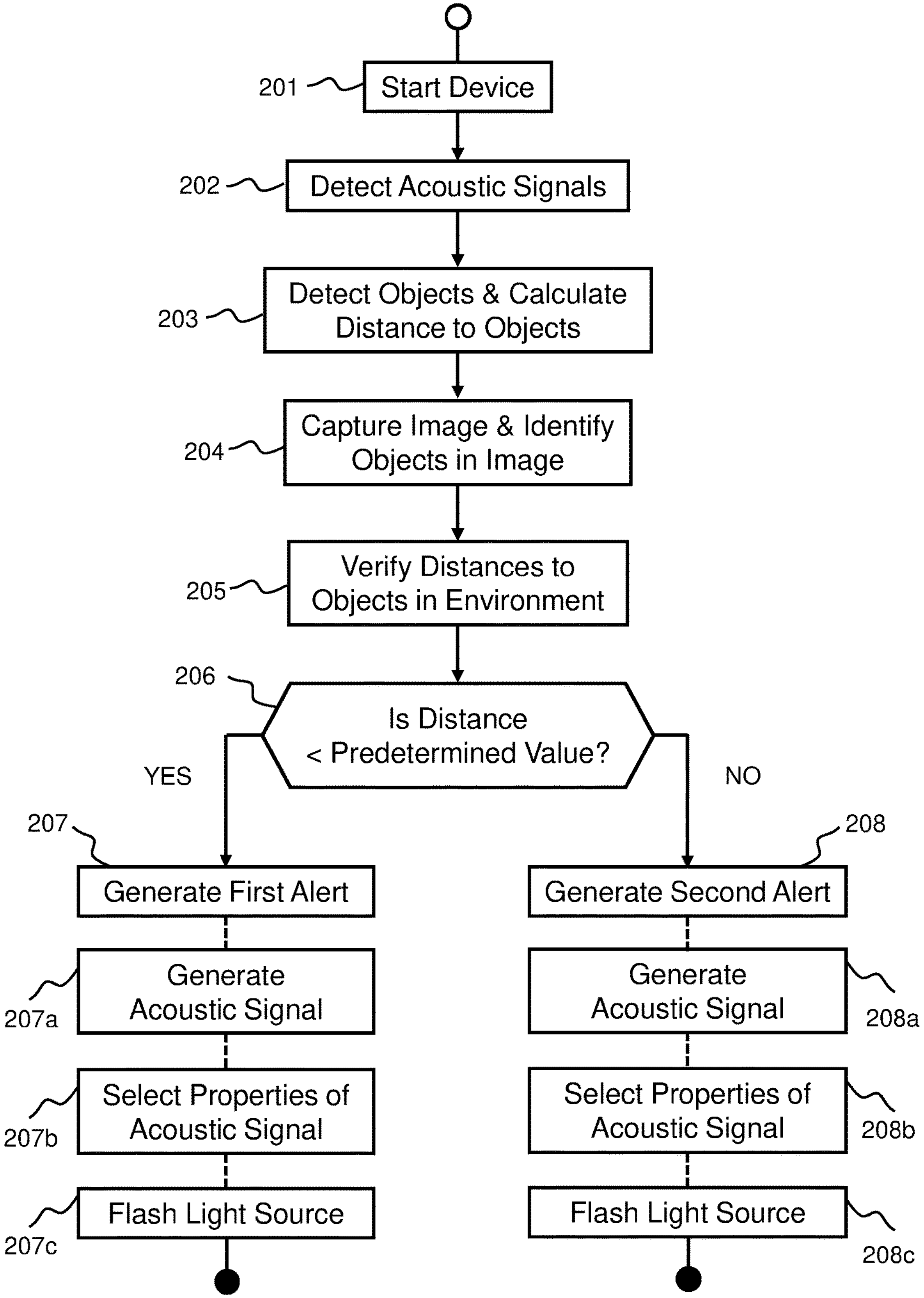
FIG. 7 is a flow chart illustrating a method of using a wearable medical device 1 according to first to third groups of embodiments.

FIG. 7 shows a flow chart indicating operation of a pair of glasses according to any of those embodiments described above. The steps of FIG. 7 are performed by the processor 10 under control of software (instructions) stored in the memory 11. In other words, the machine readable instructions, when executed by the processor, cause the processor to perform a method of using or operating the device as described herein.

In FIG. 7 the operation starts, for instance, at step 201 when the glasses are turned on or are otherwise activated. In step 202, the processor 10 controls the acoustic sensor 16 to detect environmental acoustic signals. In step 203, the processor 10 controls the spatial sensor 14 to detect objects in the environment surrounding the glasses. The distance to objects detected in the environment is calculated. In step 204, the processor 10 controls the optical sensor 17 to capture at least one image of the environment and to identify objects in the at least one image. In step 205, distances to objects in the environment are verified based on a comparison between objects identified in the images and objects detected using the spatial sensor 14. In step 206, it is determined whether the distance to an object detected in the environment is less than a predetermined value.

When it is determined that the distance is less than a predetermined value in step 206 (YES), the processor 10 controls the glasses to generate an alert at step 207. This is a first alert.

To generate the first alert, the processor 10 controls the acoustic signal generator 15 to generate an acoustic signal 207*a*. To generate the first alert, the processor 10 controls the acoustic signal generator 15 to generate the first alert having acoustic properties that are selected based on the detected environmental acoustic signals 207*b*. For instance, the first alert may be generated to have one or any combination of a volume, pitch, tone, amplitude and frequency spectrum that is based on the detected environmental acoustic signals. To generate the first alert, the processor 10 controls the light source 18 to flash 207*c*. The light source 18 flashes at a first speed. The light source 18 is intended as a visual indicator or visual feedback signal.

Figure 8:
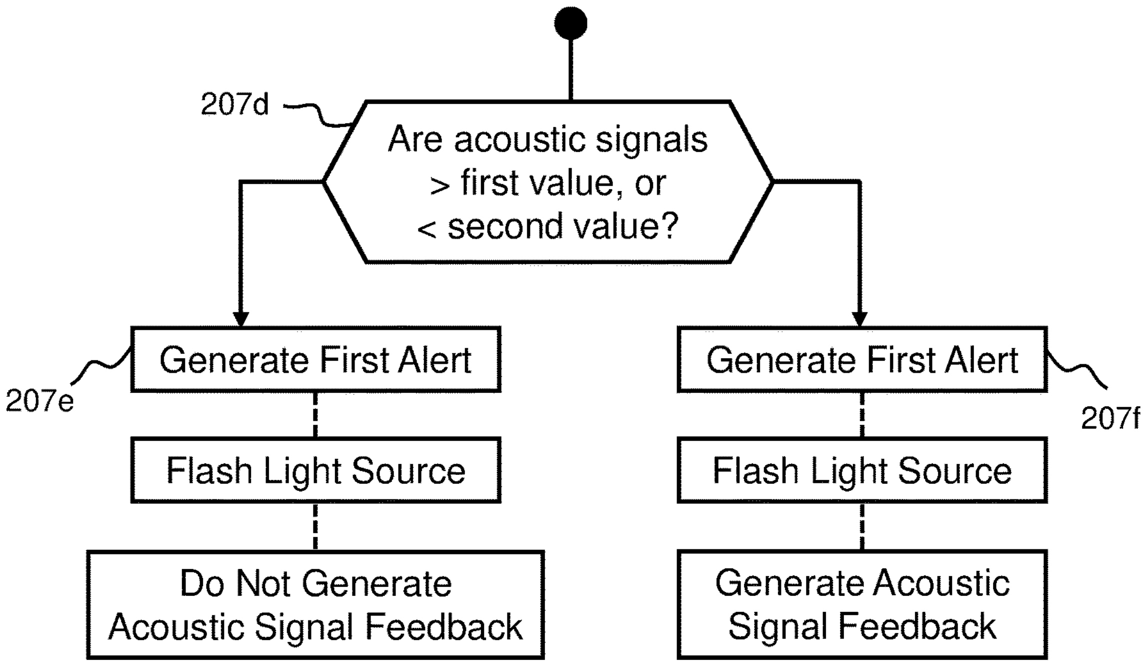
FIG. 8 is a flow chart illustrating a method of using a wearable medical device 1 according to first to third groups of embodiments.

FIG. 8 shows that, to generate the first alert, the processor 10 may also compare the acoustic signals detected in the surrounding environment by the acoustic sensor 16 with a first predetermined acoustic signal value and a second predetermined acoustic signal value, in step 207*d*. The first value represents a maximum acoustic signal value and the second value represents a minimum acoustic signal value, as described above.

When it is determined that the environmental acoustic signals are above the first value or below the second value, to generate the first alert in step 207*e*, the processor 10 controls the light source 18 to flash and prevents or does not control the acoustic signal generator 15 to generate an acoustic signal. The light source 18 flashes at a first speed.

When it is determined that the environmental acoustic signals are in the range between the first value and the second value, to generate the first alert in step 207*f*, the processor 10 controls the light source 18 to flash and controls the acoustic signal generator 15 to generate an alert. The light source 18 may flash at a first speed.

Alternatively, referring back to FIG. 7, when it is determined that the distance is greater than a predetermined value in step 206 (NO), the processor 10 controls the glasses to generate an alert 208. This alert is a second alert. The second alert is different to the first alert.

To generate the second alert, the processor 10 controls the acoustic signal generator 15 to generate an acoustic signal 208*a*. To generate the second alert, the processor 10 controls the acoustic signal generator 15 to generate the second alert having acoustic properties that are selected based on the detected environmental acoustic signals 208*b*. For instance, the second alert may be generated to have one or any combination of a volume, pitch, tone, amplitude and frequency spectrum that is based on the detected environmental acoustic signals. To generate the second alert, the processor 10 controls the light source 18 to flash 208*c*. The light source 18 flashes at a second speed.

Figure 9:
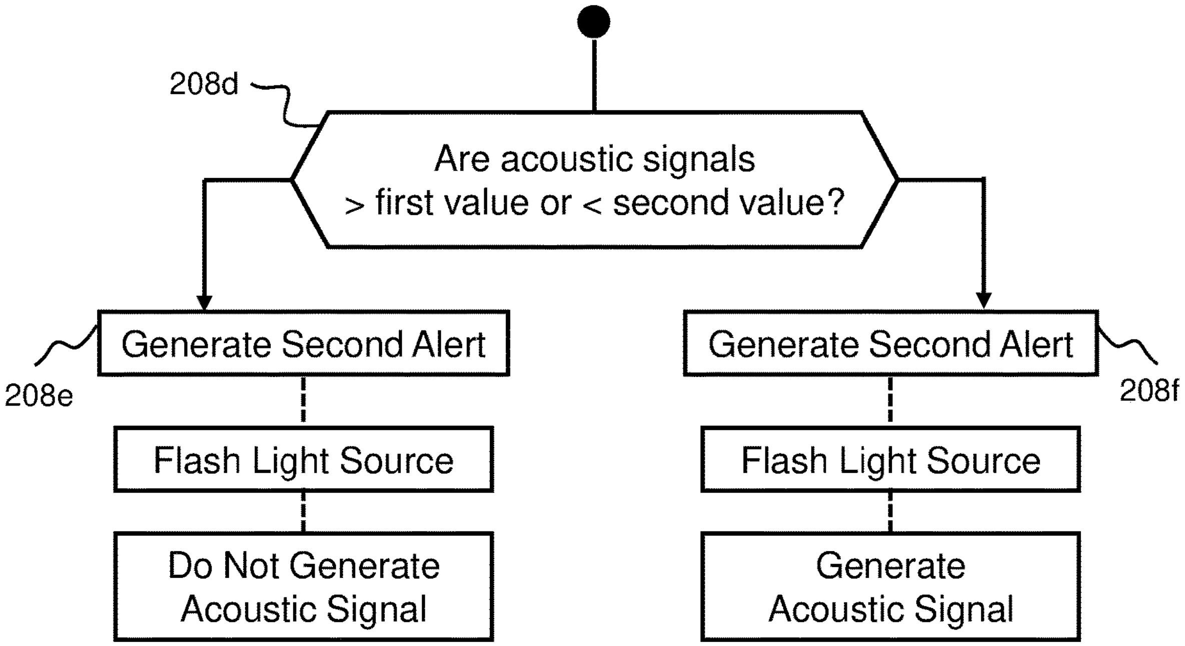
FIG. 9 is a flow chart illustrating a method of using a wearable medical device 1 according to first to third groups of embodiments.

FIG. 9 shows that, to generate the second alert, the processor 10 may also compare the acoustic signals detected in the surrounding environment by the acoustic sensor 16 with a first predetermined acoustic signal value and a second predetermined acoustic signal value, in step 208*d*. The first value represents a maximum acoustic signal value and the second value represents a minimum acoustic signal value, as described above.

When it is determined that the environmental acoustic signals are above a first value or below a second value, to generate the second alert in step 208*e*, the processor 10 controls the light source 18 to flash and prevents or does not control the acoustic signal generator 15 to generate an acoustic signal. The light source 18 may flash at a second speed.

When it is determined that the environmental acoustic signals are in the range between the first value and the second value, to generate the second alert in step 208*f*, the processor 10 controls the light source 18 to flash and controls the acoustic signal generator 15 to generate an alert. The light source 18 flashes at a second speed.

In the above, steps 202, 204, 205, 207*b-f*, 208*b-f*, relate to optional components of the wearable medical device 1. Thus, the inclusion of steps 202, 204, 205, 207*b-f*, 208*b-f* is optional and one or more of these steps may be omitted. For instance, one or more of these steps may be omitted where the wearable medical device 1 does not include the corresponding electronic component required to perform that step.

Figure 10:
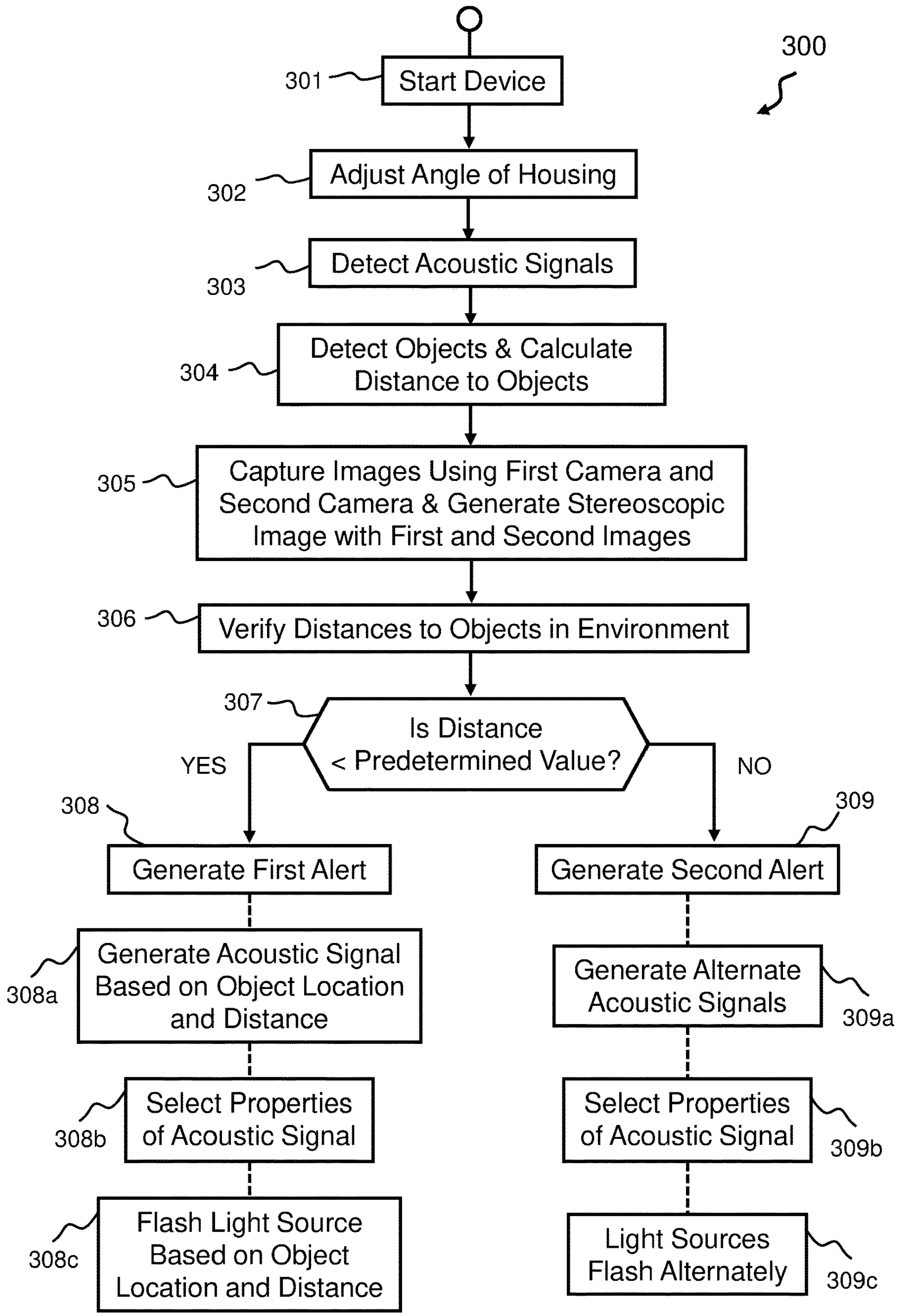
FIG. 10 is a flow chart illustrating a method of using a wearable medical device 1 according to second and third groups of embodiments.

FIG. 10 shows a flow chart indicating operation of a pair of glasses according to the second or third group of embodiments as shown in FIGS. 3 to 6. The steps of FIG. 10 are performed by the processor 10 under control of software (instructions) stored in the memory 11.

In FIG. 10 the operation starts, for instance, at step 301 when the glasses are turned on or are otherwise activated. In step 302, the processor 10 controls the actuator to rotate one or more housings 7 to an angle that is horizontal. That is, the processor 10 controls the actuator to adjust the angle of the housing 7 to provide a horizontal view based on the body posture of the user. In step 303, the processor 10 controls the acoustic sensor 16 to detect environmental acoustic signals. In step 304, the processor 10 controls the spatial sensor 14 to detect objects in the environment surrounding the glasses. The distance to objects detected in the environment is calculated. In step 305, the processor 10 controls the operation of first and second optical sensor 17, each located in a housing 7 on either side of the glasses. The processor 10 controls the first optical sensor 17 to capture at least one image of the environment from a first position on one side of the glasses, and at the same time, controls the second optical sensor 17 to capture at least one image of the environment from a second position on the other side of the glasses. The processor 10 generates a stereoscopic image of the environment based on the images captured by the first optical sensor 17 and the second optical sensor 17. In step 306, distances to objects in the environment are verified based on a comparison between objects identified in the stereoscopic image and objects detected using the spatial sensor 14. In step 307, it is determined whether the distance to an object detected in the environment is less than a predetermined value.

When it is determined that the distance is less than a predetermined distance value in step 307 (YES), the processor 10 controls the glasses to generate an alert in step 308. This is a first alert.

To generate the first alert, the processor 10 controls the pair of acoustic signal generators 15, one acoustic signal generator 15 provided on each side of the glasses, to generate an acoustic signal 308*a*. The processor 10 controls the acoustic signal generator 15 located on the side of the glasses nearest to the object that is detected at a distance less than the predetermined value to generate an alert. In particular, the processor 10 controls the acoustic signal generator 15 located on the left side to generate an alert when an object is identified in the environment to the left of the glasses. The processor 10 controls the acoustic signal generator 15 on the right side to generate an alert when an object is identified in the environment to the right of the glasses. The processor 10 controls the pair of acoustic signal generators 15 (that is the acoustic signal generator 15 on the left side and the acoustic signal generator 15 on the right side) to generate an alert when an object is identified in the environment in front of the glasses. The alert is an intermittent click, but could equally well be a beep, a chirp, or the like.

The processor 10 controls the pair of acoustic signal generators 15 so that the time between each acoustic signal generated varies in accordance with (e.g. is directly proportional to) the detected distance that the object is less than the predetermined distance. As the distance to the object decreases further, the time between clicks also decreases. This means that as the user approaches an object the time between intermittent clicks decreases until a continuous click is generated. This occurs when the user is in contact with or is about to contact the object. If the distance does not decrease further then the time between clicks remains the same.

To generate the first alert, the processor 10 controls the pair of acoustic signal generators 15 to generate the first alert having acoustic properties that are selected based on detected environmental acoustic signals 308*b*. For instance, the first alert is generated to have one or any combination of a volume, pitch, tone, amplitude and frequency spectrum that is based on the detected environmental acoustic signals.

At the same time, to generate the first alert, the processor 10 controls the pair of light sources 18, one provided on each side of the glasses, to flash 308*c*. The processor 10 controls the light source 18 located on the side of the glasses nearest to the object that is detected at a distance less than the predetermined value to flash. In particular, the processor 10 controls the light source 18 located on the left side to flash when an object is identified in the environment to the left of the glasses. The processor 10 controls the light source 18 on the right side to flash when an object is identified in the environment to the right of the glasses. The processor 10 controls the light source 18 on the left side and the light source 18 on the right side to flash when an object is identified in the environment in front of the glasses.

The processor 10 controls the pair of light sources 18 so that the time between each flash generated varies in accordance with (e.g. is directly proportional to) the detected distance that the object is less than the predetermined distance. As the distance to the object decreases further, the time between flashes also decreases. This means that as the user approaches an object the time between each flash decreases until the light source 18 is turned on continuously or the light source 18 and/or changes colour. This occurs when the user is in contact with or is about to contact the object. If the distance does not decrease further then the time between flashes remains the same.

Alternatively, in FIG. 10, when it is determined that the distance is greater than a predetermined value in step 307 (NO), the processor 10 controls the glasses to generate an alert in step 309. This alert is a second alert. The second alert is different to the first alert.

To generate the second alert, the processor 10 controls the pair of acoustic signal generators 15, one provided on either side of the glasses, to generate an acoustic signal as the second alert 309*a*. The acoustic signal is output intermittently. The processor 10 controls each pair of acoustic signal generators 15 on either side of the glasses to alternately generate an alert. In other words, when the pair of acoustic signal generators 15 on the left side generates an alert, the pair of acoustic signal generators 15 on the right side does not, and vice versa. The alert is a click, but may equally well be a beep, a chirp, or the like.

To generate the second alert, the processor 10 controls the acoustic signal generator 15 to generate the second alert having acoustic properties that are selected based on detected environmental acoustic signals 309*b*. For instance, the second alert is generated to have one or any combination of a volume, pitch, tone, amplitude and frequency spectrum that is based on the detected environmental acoustic signals.

To generate the second alert, the processor 10 controls a pair of light sources 18, one on each side of the glasses, to flash 309*c*. The light sources 18 flash at a second speed. The processor controls each pair of light sources 18 to flash alternately between one side of the glasses and the other. In other words the pair of light sources 18 on the left side flashes on when the pair of light sources 18 on the right side flashes off, and vice versa.

In the above, steps 302, 305, 308*b-c*, 309*b-c*, relate to optional components of the wearable medical device 1. Thus, the inclusion of steps 302, 305, 308*b-c*, 309*b-c*, is optional and one or more of these steps may be omitted. For instance, one or more of these steps may be omitted where the wearable medical device 1 does not include the corresponding electronic component required to perform that step.

The operations of the wearable medical device 1 described above provide an alert that indicates to the user the presence of an object in the surrounding environment that is within a predetermined distance. The following operations of the wearable medical device 1 are associated with the handling and management of a drug delivery device, such as an injection device. The injection device may be, for instance, an injection pen.

Figure 11:
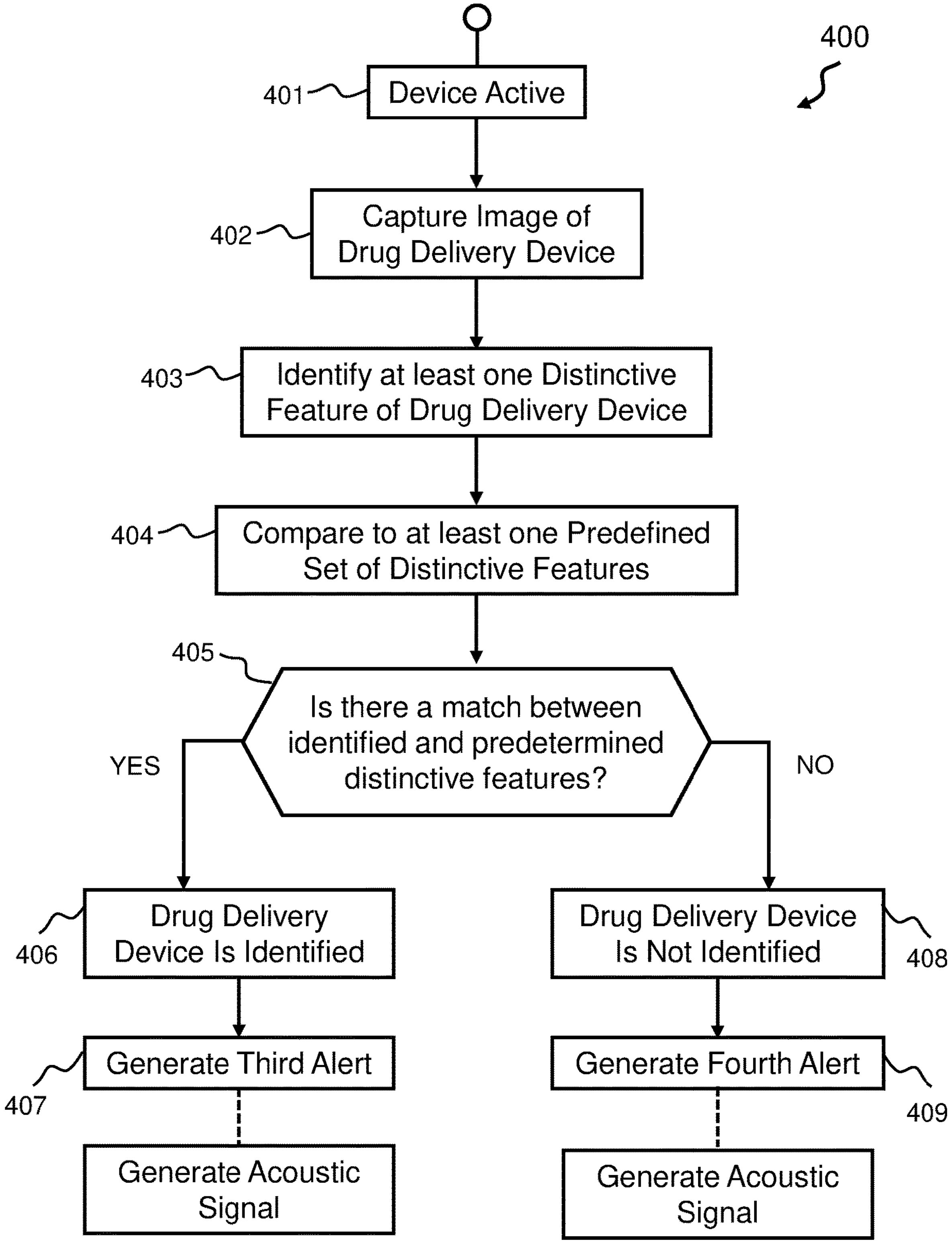
FIG. 11 is a flow chart illustrating a method of using a wearable medical device 1 according to a fourth group of embodiments.

FIG. 11 shows a flow chart indicating operation of a pair of glasses 400 according to a fourth group of embodiments. The steps of FIG. 11 are performed by a processor 10 under control of software (instructions) stored in the memory 11. Here, the memory 11 stores at least one predefined set of distinctive features associated with a drug delivery device. The predefined set of distinctive features identify a status of the drug delivery device, including one or more of: a type of drug delivery device, a medicament loaded in the drug delivery device, a dose dialed at the drug delivery device, an ejection of a dose from the drug delivery device. The glasses 400 comprise an optical sensor 17, in addition to a spatial sensor 14 and an acoustic signal generator 15.

In FIG. 11, the operation starts at step 401 when the glasses 400 are turned on or are otherwise activated. In step 402, the processor 10 controls the optical sensor 17 to capture at least one image of a drug delivery device. In step 403, at least one distinctive feature of the drug delivery device is identified in the image. In step 404, the at least one distinctive feature is compared to the at least one predefined set of distinctive features stored in the memory 11. In step 405, it is determined whether or not there is a match between the at least one distinctive feature of the drug delivery device and the at least one predefined set of distinctive features.

In step 406, the drug delivery device is identified when it is determined that there is a match of the at least one distinctive feature of the drug delivery device with at least one distinctive feature of the predefined set of distinctive features. In step 407, the processor 10 controls the acoustic signal generator 15 to generate an alert. The alert is a third alert.

Alternatively, in step 408, the drug delivery device is not identified, when it is determined that there is no match of the at least one distinctive feature of the drug delivery device with at least one distinctive feature of the predefined set of distinctive features. In step 409, the processor 10 controls the acoustic signal generator 15 to generate an alert. This is a fourth alert. The fourth alert is different to the third alert.

The third alert and the fourth alert provide acoustic feedback to the user as to whether the correct drug delivery device has been selected. In other words, whether the user is handling the correct drug delivery device intended for use by the user. Thus, acoustic signal of the third alert is generated as a positive or confirmatory alert, whereas the acoustic signal of the fourth alert is generated as a negative or adverse alert.

Figure 12:
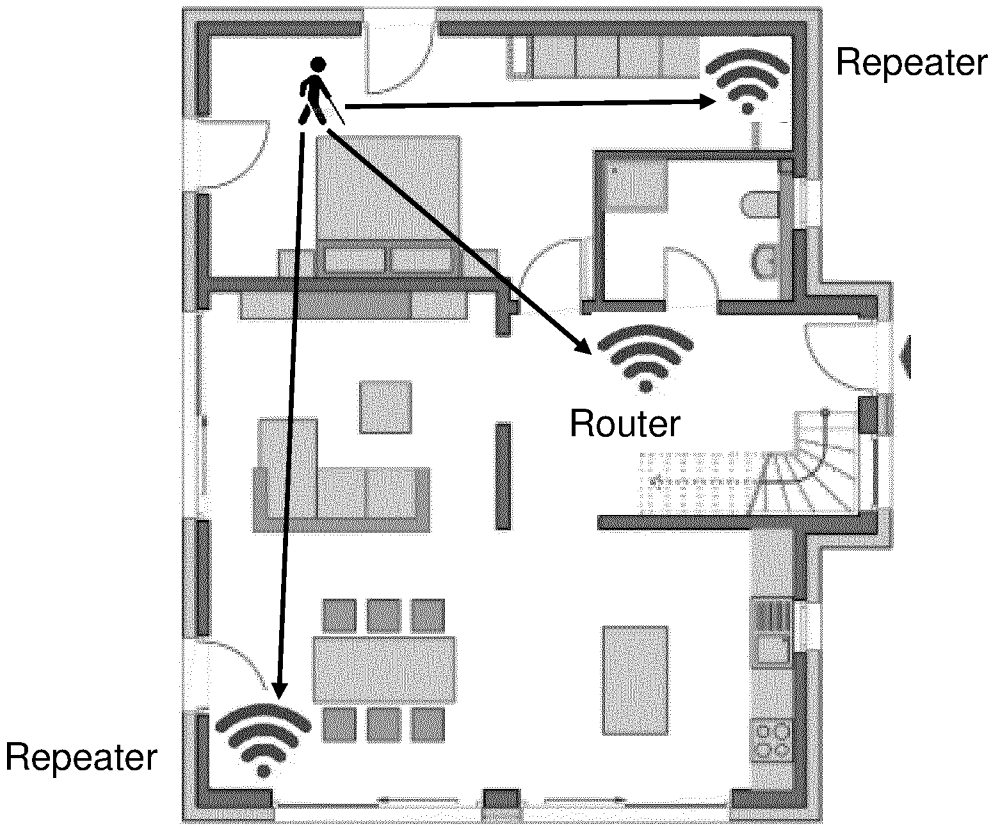
FIG. 12 is a plan view of a floor plan in of a home environment according to a fifth group of embodiments.

FIG. 12 shows a schematic drawing indicating operation of a pair of glasses 500 according to a fifth group of embodiments. In particular, the following operations relate to the use of the glasses 500 as a home assistant in a home environment. Here, the glasses 500 comprise at least the spatial sensor 14, the acoustic signal generator 15, the optical sensor 17, and the wireless unit 20.

Figure 13A:
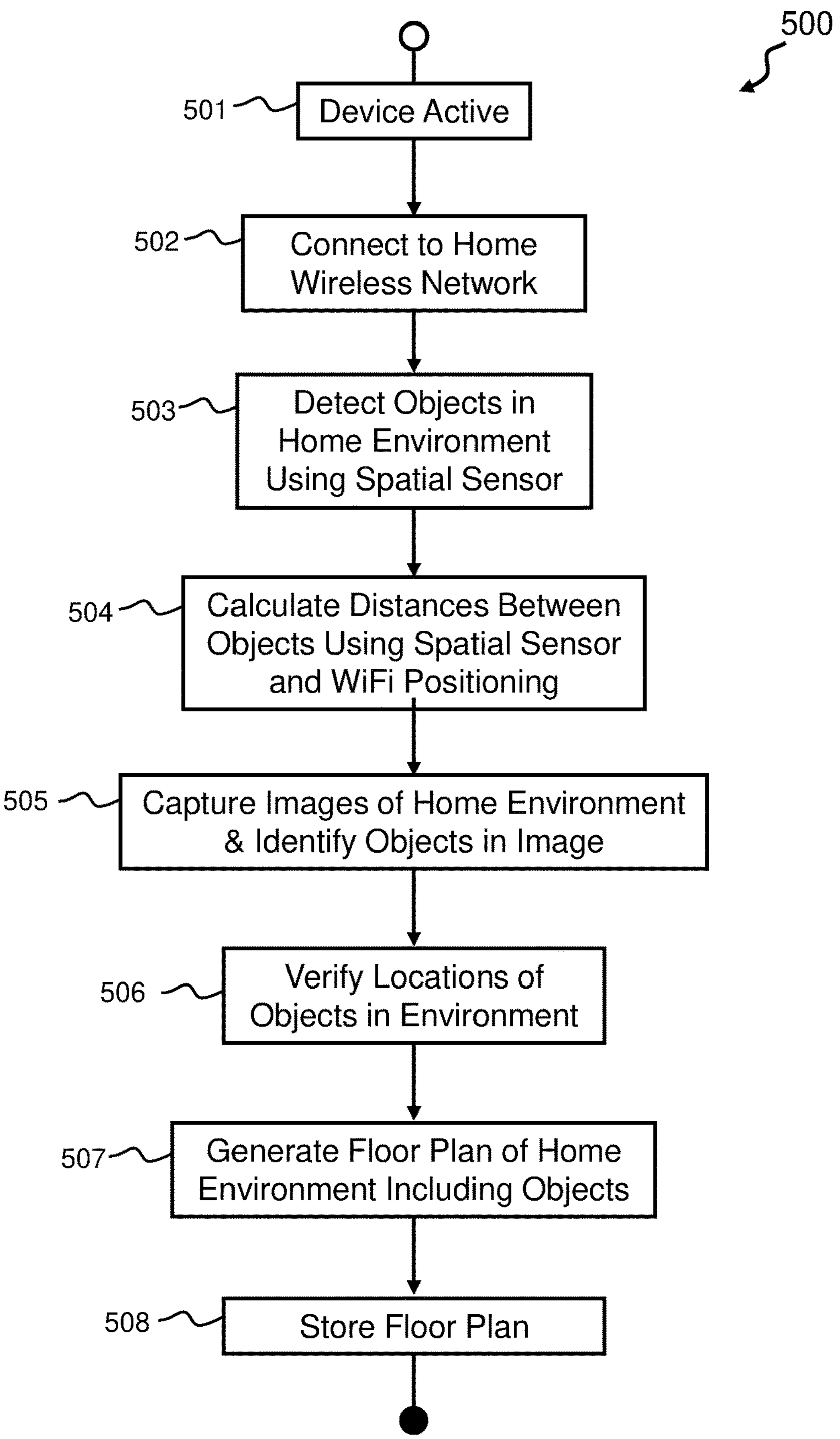
FIG. 13A is a flow chart illustrating a method of using a wearable medical device 1 according to the fifth group of embodiments.

FIG. 13A shows a flow chart indicating operation of a pair of glasses 500 according to the fifth group of embodiments. The steps of FIG. 13A are performed by the processor 10 under control of software (instructions) stored in the memory 11. For instance, under the control of a home assistant application 13 stored in the memory 11.

In FIG. 13A the operation starts, for instance, at step 501 when the glasses 500 are turned on or are otherwise activated. In step 502, the processor 10 identifies a wireless network as a user home network and controls the wireless unit 20 to establish a connection to the wireless network in the home environment. This may occur as the user enters the home environment, as shown in FIG. 12. In step 503, the processor 10 controls the spatial sensor 14 to detect objects in the home environment. In step 504, distances between objects detected in the environment are calculated using the spatial sensor 14 and WiFi positioning using the home network. In step 505, the processor 10 controls the optical sensor 17 to capture images of the home environment. Objects in the images of the home environment are identified. In step 506, locations of objects in the environment are verified based on the objects identified in the images and distances between objects calculated using the spatial sensor 14 and WiFi positioning. In step 507, a floor plan representing the home environment including the objects is generated. FIG. 12 shows an exemplary floor plan of the home environment. In step 508, the floor plan is stored in the memory 11.

Figure 13B:
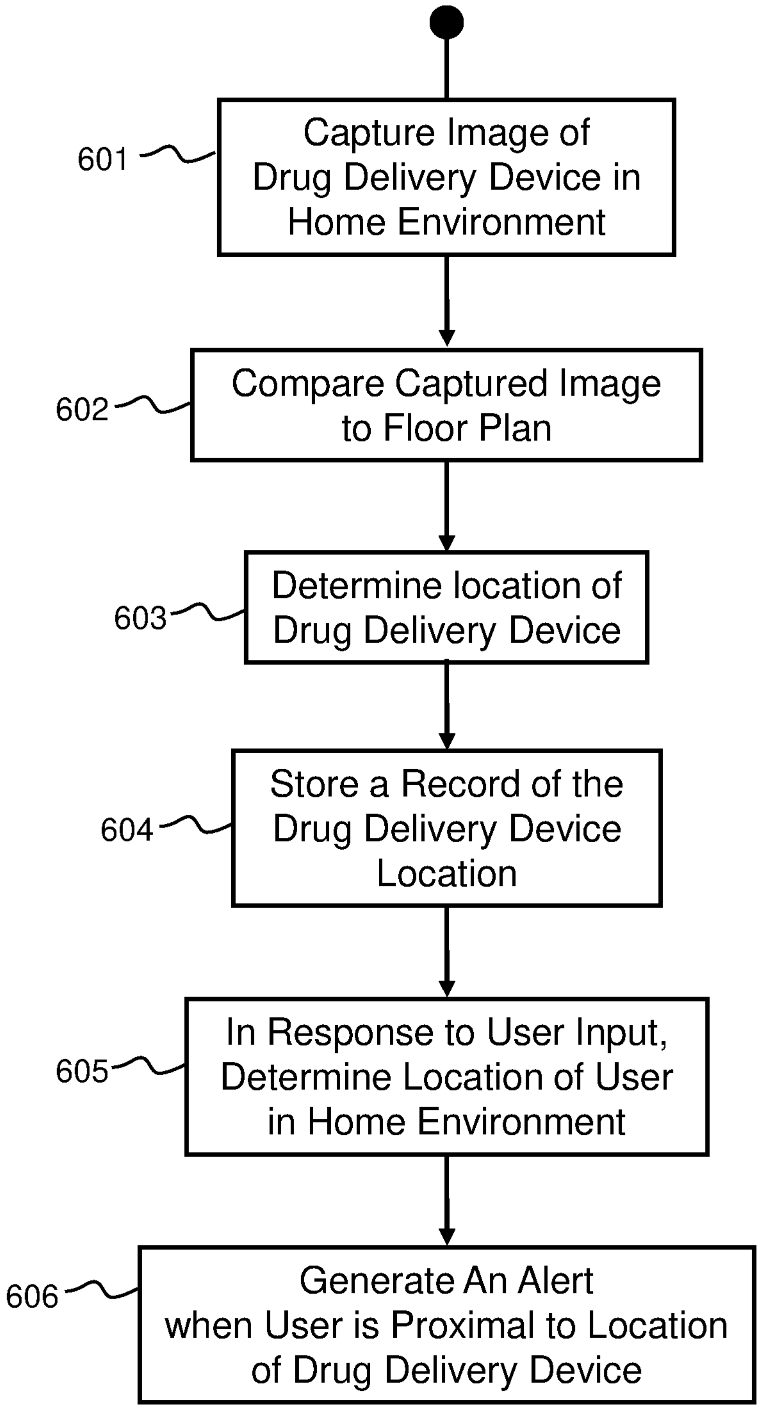
FIG. 13B is a flow chart illustrating a method of using a wearable medical device 1 according to the fifth group of embodiments.

FIG. 13B shows a flow chart indicating the further operation of the glasses 500 as a home assistant, if the user requires the use of a drug delivery device. Here, the operation of the glasses 500 helps the user to find a medical device or other things by monitoring of the last location of use (storage location).

In FIG. 13B, in step 601, processor 10 controls the optical sensor 17 to capture an image of a drug delivery device in the home environment. In step 602, the processor 10 compares the image of the home environment including the drug delivery device to the floor plan. In step 603, based on the comparison the location of the drug delivery device in the image of the home environment is determined. In step 604, a record of the location of the drug delivery device in the home environment is stored in the memory 11. In step 605, in response to a user input, the processor 10 determines the location of the user in relation to the floor plan using the spatial sensor 14, WiFi positioning and the optical sensor 17. In step 606, the processor 10 controls the acoustic signal generator 15 to generate an alert when the user is proximal to the location of the drug delivery device based on the record of the location of the drug delivery device.

This operation provides an acoustic feedback signal to the user to indicate when the user is proximal to the location of the drug delivery device, based on the last stored record of the location of the drug delivery device. The above operation of the wearable medical device 1 helps the user to locate the drug delivery device in the home environment.

Various alternatives and modifications to the embodiments shown and described above will be apparent to those skilled in the art. For instance, it will be appreciated that not all components are essential and a person skilled in the art may choose to omit one or more components from the wearable medical device 1. Similarly, it will be evident that compatible features (one or more) of different embodiments may be combined. Some such variations and modifications will now be described.

The glasses have been shown to include a number of components arranged in a particular configuration, however, the present disclosure is not limited to such an arrangement. Alternative arrangements may equally well be implemented with respect to the wearable medical device 1. For instance, at least one of one or any combination of these components may equally well be accommodated at the wearable medical device 1.

A pair of housings 7 is described with respect to FIGS. 3 and 4, but could equally well be implemented with one housing 7. Similarly, the embodiments disclosed with respect to FIGS. 5 and 6, could be implemented in one or two housings 7.

Various operations have been described when it is detected that objects are less than a predetermined distance or greater than a predetermined distance from the wearable medical device 1. The provision of both options is not essential and the wearable medical device 1 may equally well function only according to operations where it is detected that objects are less than a predetermined distance from the wearable medical device 1.

In respect of FIG. 10, the angle of the housing 7 is described as being orientated to horizontal, however the present disclosure is not limited to this. The angle of the housing 7 could equally well be orientated to any angle appropriate to the requirements of the user.

A home network is described in relation to FIGS. 12 and 13, but the wireless network may equally well be an office environment or other environment designated by the user for the purpose of operating the wearable medical device 1. An associated floor plan may then be generated for that designated environment.

Embodiments of the present disclosure have been described with reference to a pair of glasses. The present disclosure is not, however, limited to a pair of glasses and the wearable medical device 1 may equally well be implemented in an alternative device, such as a head band, an arm band, a hat or a mobile device, such as a smart phone.

The drug delivery device has been disclosed as an injection device, but the present disclosure is not limited to this. The drug delivery device may equally well be another type of drug delivery device, such as a bolus injector.

The present disclosure is not limited to monitoring the last location of a drug delivery device, but could equally well be configured to monitor the location of any suitable object relevant to the user.

Although the present disclosure has been shown and described according to the above embodiments, it would be appreciated by those skilled in the art that changes may be made to the subject matter described herein without departing from the present disclosure, the scope of which is defined in the claims.

The terms "drug" or "medicament" are used synonymously herein and describe a pharmaceutical formulation containing one or more active pharmaceutical ingredients or pharmaceutically acceptable salts or solvates thereof, and optionally a pharmaceutically acceptable carrier. An active pharmaceutical ingredient ("API"), in the broadest terms, is a chemical structure that has a biological effect on humans or animals. In pharmacology, a drug or medicament is used in the treatment, cure, prevention, or diagnosis of disease or used to otherwise enhance physical or mental well-being. A drug or medicament may be used for a limited duration, or on a regular basis for chronic disorders.

As described below, a drug or medicament can include at least one API, or combinations thereof, in various types of formulations, for the treatment of one or more diseases. Examples of API may include small molecules having a molecular weight of 500 Da or less; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more drugs are also contemplated.

The drug or medicament may be contained in a primary package or "drug container" adapted for use with a drug delivery device. The drug container may be, e.g., a cartridge, syringe, reservoir, or other solid or flexible vessel configured to provide a suitable chamber for storage (e.g., short- or long-term storage) of one or more drugs. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of the pharmaceutical formulation to-be-administered (e.g., an API and a diluent, or two different drugs) separately, one in each chamber. In such instances, the two chambers of the dual-chamber cartridge may be configured to allow mixing between the two or more components prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drugs or medicaments contained in the drug delivery devices as described herein can be used for the treatment and/or prophylaxis of many different types of medical disorders. Examples of disorders include, e.g., diabetes mellitus or complications associated with diabetes mellitus such as diabetic retinopathy, thromboembolism disorders such as deep vein or pulmonary thromboembolism. Further examples of disorders are acute coronary syndrome (ACS), angina, myocardial infarction, cancer, macular degeneration, inflammation, hay fever, atherosclerosis and/or rheumatoid arthritis. Examples of APIs and drugs are those as described in handbooks such as Rote Liste 2014, for example, without limitation, main groups 12 (anti-diabetic drugs) or 86 (oncology drugs), and Merck Index, 15th edition.

Examples of APIs for the treatment and/or prophylaxis of type 1 or type 2 diabetes mellitus or complications associated with type 1 or type 2 diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the terms "analogue" and "derivative" refers to a polypeptide which has a molecular structure which formally can be derived from the structure of a naturally occurring peptide, for example that of human insulin, by deleting and/or exchanging at least one amino acid residue occurring in the naturally occurring peptide and/or by adding at least one amino acid residue. The added and/or exchanged amino acid residue can either be codable amino acid residues or other naturally occurring residues or purely synthetic amino acid residues. Insulin analogues are also referred to as "insulin receptor ligands". In particular, the term "derivative" refers to a polypeptide which has a molecular structure which formally can be derived from the structure of a naturally occurring peptide, for example that of human insulin, in which one or more organic substituent (e.g. a fatty acid) is bound to one or more of the amino acids. Optionally, one or more amino acids occurring in the naturally occurring peptide may have been deleted and/or replaced by other amino acids, including non-codeable amino acids, or amino acids, including non-codeable, have been added to the naturally occurring peptide.

Examples of insulin analogues are Gly(A21), Arg(B31), Arg(B32) human insulin (insulin glargine); Lys(B3), Glu (B29) human insulin (insulin glulisine); Lys(B28), Pro(B29) human insulin (insulin lispro); Asp(B28) human insulin (insulin aspart); human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Examples of insulin derivatives are, for example, B29-N-myristoyl-des(B30) human insulin, Lys(B29) (N-tetradecanoyl)-des(B30) human insulin (insulin detemir, Levemir®); B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-gamma-glutamyl)-des(B30) human insulin, B29-N-omega-carboxypentadecanoyl-gamma-L-glutamyl-des(B30) human insulin (insulin degludec, Tresiba®); B29-N-(N-lithocholyl-gamma-glutamyl)-des(B30) human insulin; B29-N-(ω-carboxyheptadecanoyl)-des(B30) human insulin and B29-N-(w-carboxyheptadecanoyl) human insulin.

Examples of GLP-1, GLP-1 analogues and GLP-1 receptor agonists are, for example, Lixisenatide (Lyxumia®), Exenatide (Exendin-4, Byetta®, Bydureon®, a 39 amino acid peptide which is produced by the salivary glands of the Gila monster), Liraglutide (Victoza®), Semaglutide, Taspoglutide, Albiglutide (Syncria®), Dulaglutide (Trulicity®), rExendin-4, CJC-1134-PC, PB-1023, TTP-054, Langlenatide/HM-11260C (Efpeglenatide), HM-15211, CM-3, GLP-1 Eligen, ORMD-0901, NN-9423, NN-9709, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, ZP-DI-70, TT-401 (Pegapamodtide), BHM-034. MOD-6030, CAM-2036, DA-15864, ARI-2651, ARI-2255, Tirzepatide (LY3298176), Bamadutide (SAR425899), Exenatide-XTEN and Glucagon-Xten.

An example of an oligonucleotide is, for example: mipomersen sodium (Kynamro®), a cholesterol-reducing antisense therapeutic for the treatment of familial hypercholesterolemia or RG012 for the treatment of Alport syndrom.

Examples of DPP4 inhibitors are Linagliptin, Vildagliptin, Sitagliptin, Denagliptin, Saxagliptin, Berberine.

Examples of hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Examples of polysaccharides include a glucosaminoglycane, a hyaluronic acid, a heparin, a low molecular weight heparin or an ultra-low molecular weight heparin or a derivative thereof, or a sulphated polysaccharide, e.g., a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20 (Synvisc®), a sodium hyaluronate.

The term "antibody", as used herein, refers to an immunoglobulin molecule or an antigen-binding portion thereof. Examples of antigen-binding portions of immunoglobulin molecules include F(ab) and F(ab')2 fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region. The term antibody also includes an antigen-binding molecule based on tetravalent bispecific tandem immunoglobulins (TBTI) and/or a dual variable region antibody-like binding protein having cross-over binding region orientation (CODV).

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full-length antibody polypeptide, although the term is not limited to such cleaved fragments. Antibody fragments that are useful in the present disclosure include, for example, Fab fragments, F(ab')2 fragments, scFv (single-chain Fv) fragments, linear antibodies, monospecific or multispecific antibody fragments such as bispecific, trispecific, tetraspecific and multispecific antibodies (e.g., diabodies, triabodies, tetrabodies), monovalent or multivalent antibody fragments such as bivalent, trivalent, tetravalent and multivalent antibodies, minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Examples of antibodies are anti PCSK-9 mAb (e.g., Alirocumab), anti IL-6 mAb (e.g., Sarilumab), and anti IL-4 mAb (e.g., Dupilumab).

Pharmaceutically acceptable salts of any API described herein are also contemplated for use in a drug or medicament in a drug delivery device. Pharmaceutically acceptable salts are for example acid addition salts and basic salts.

Those of skill in the art will understand that modifications (additions and/or removals) of various components of the APIs, formulations, apparatuses, methods, systems and embodiments described herein may be made without departing from the full scope and spirit of the present invention, which encompass such modifications and any and all equivalents thereof.

An example drug delivery device may involve a needle-based injection system as described in Table 1 of section 5.2 of ISO 11608-1: 2014(E). As described in ISO 11608-1: 2014(E), needle-based injection systems may be broadly distinguished into multi-dose container systems and single-dose (with partial or full evacuation) container systems. The container may be a replaceable container or an integrated non-replaceable container.

As further described in ISO 11608-1:2014(E), a multi-dose container system may involve a needle-based injection device with a replaceable container. In such a system, each container holds multiple doses, the size of which may be fixed or variable (pre-set by the user). Another multi-dose container system may involve a needle-based injection device with an integrated non-replaceable container. In such a system, each container holds multiple doses, the size of which may be fixed or variable (pre-set by the user).

As further described in ISO 11608-1:2014(E), a single-dose container system may involve a needle-based injection device with a replaceable container. In one example for such a system, each container holds a single dose, whereby the entire deliverable volume is expelled (full evacuation). In a further example, each container holds a single dose, whereby a portion of the deliverable volume is expelled (partial evacuation). As also described in ISO 11608-1:2014 (E), a single-dose container system may involve a needle-based injection device with an integrated non-replaceable container. In one example for such a system, each container holds a single dose, whereby the entire deliverable volume is expelled (full evacuation). In a further example, each container holds a single dose, whereby a portion of the deliverable volume is expelled (partial evacuation).

The invention claimed is:

1. A wearable medical device comprising:

a spatial sensor configured to determine distance to objects in an environment in front of the spatial sensor;

an acoustic signal generator operable to generate an acoustic signal;

an acoustic sensor configured to detect environmental acoustic signals;

a light source;

a processor; and a memory configured to store instructions which, when executed the processor, cause the wearable medical device to:

detect, using the spatial sensor, the objects in the environment, calculate the distance to the objects detected in the environment, determine that the distance to an object is less than a predetermined value, control the acoustic signal generator to generate a first alert, control the acoustic sensor to detect environmental acoustic signals, control the acoustic signal generator to generate alerts having acoustic properties that are selected based on the environmental acoustic signals detected, determine that the acoustic sensor detected environmental acoustic signals, and control the light source to flash and actuate or prevent the acoustic signal generator from generating the acoustic signal based on a value of the environmental acoustic signals relative to a first predetermined value and a second predetermined value.

2. The wearable medical device of claim 1, wherein the instructions when executed by the processor further cause the wearable medical device to:

determine that the distance to the object is greater than the predetermined value; and control the acoustic signal generator to generate a second alert, wherein the second alert is different to the first alert.

3. The wearable medical device of claim 1, wherein the acoustic signal generator comprises a pair of acoustic signal generators, one acoustic signal generator of the pair of acoustic signal generators being provided on each side of the wearable medical device, and wherein the instructions when executed by the processor, further cause the wearable medical device to:

determine that the distance to the object is greater than the predetermined value; and control the pair of acoustic signal generators to generate an alert alternately on each side of the wearable medical device.

4. The wearable medical device of claim 1, wherein the acoustic sensor comprises a moving coil, a dynamic microphone, a condenser microphone or a piezoelectric microphone.

5. The wearable medical device of claim 1, wherein the light source comprises a light emitting diode emitting a monochromatic or polychromatic and/or a time sequenced light, and wherein the instructions when executed by the processor, further cause the wearable medical device to:

determine that the acoustic sensor detects the environmental acoustic signals above the first predetermined value or below the second predetermined value and control the light source to flash and prevent the acoustic signal generator from generating the acoustic signal, and determine that the acoustic sensor detects the environmental acoustic signals in a range between the first predetermined value and the second predetermined value and control the light source to flash and the acoustic signal generator to generate an alert.

6. The wearable medical device of claim 1, further comprising an optical sensor configured to capture images of the environment, wherein the instructions when executed the processor, further cause the wearable medical device to:

capture, using the optical sensor, at least one image of the environment, identify, in the at least one image, the objects in the environment, and verify distances of the objects in the environment based on a comparison with the objects detected in the environment using the spatial sensor.

7. The wearable medical device of claim 1, wherein the instructions when executed by the processor, further cause the wearable medical device to:

determine that the distance to the object is greater than the predetermined value, control the light source to flash at a first speed, determine that the distance to the object is less than the predetermined value, and control the light source to flash at a second speed.

8. The wearable medical device of claim 7, wherein the light source further comprises a pair of light sources, one light source of the pair of light sources being provided on each side of the wearable medical device, and wherein the instructions when executed by the processor, further cause the wearable medical device to:

control the light source on a left side to flash in response to determining that the object is identified in the environment to the left side of the wearable medical device and the distance to the object is less than the predetermined value, control the light source on a right side to flash in response to determining that the object is identified in the environment to the right side of the wearable medical device and the distance to the object is less than the predetermined value, control the light source on the left side and the light source on the right side to flash in response to determining that the object is identified in the environment in front of the wearable medical device and the distance to the object is less than a predetermined value, and control the light source on the left side and the light source on the right side to flash alternately in response to determining that the distance to the object is greater than the predetermined value.

9. The wearable medical device of claim 1, wherein the instructions when executed by the processor, further cause the wearable medical device to:

control a first acoustic signal generator on a left side to generate an alert in response to determining that the object is identified in the environment to the left side of the wearable medical device and the distance to the object is less than a predetermined value, control a second acoustic signal generator on a right side to generate an alert in response to determining that the object is identified in the environment to the right side of the wearable medical device and the distance to the object is less than a predetermined value, and control the first acoustic signal generator on the left side and the second acoustic signal generator on the right side to generate an alert in response to determining that the object is identified in the environment in front of the wearable medical device and the distance to the object is less than a predetermined value.

10. The wearable medical device of claim 1, further comprising a housing that is pivotally mounted to a side of the wearable medical device, the housing comprising at least one sensor and an actuator configured to pivot the housing with respect to device, wherein the instructions when executed by the processor, further cause the wearable medical device to:

control the actuator to adjust an orientation of the housing to an angle that is horizontal with respect to a body posture of a user.

11. The wearable medical device of claim 10, wherein the housing comprises a pair of housings, a first housing being located on a first side of the wearable medical device and a second housing being located on a second side of the wearable medical device, wherein the first housing comprises a first optical sensor and the second housing comprises a second optical sensor, and wherein the instructions when executed by the processor, further cause the wearable medical device to:

control the first optical sensor to capture a first image of the environment from a first position on the first side of the wearable medical device, control the second optical sensor to capture a second image of the environment from a second position on the second side of the wearable medical device, and process the first image and the second image to generate a stereoscopic image.

12. The wearable medical device of claim 1, further comprising an optical sensor configured to capture images of the environment, wherein the instructions when executed by the processor, further cause the wearable medical device to:

capture, using the optical sensor, at least one image of the environment;

identify, in the at least one image, a drug delivery device selected for use by a user of the wearable medical device; and control the acoustic signal generator to generate a second alert.

13. The wearable medical device of claim 12, wherein the drug delivery device is configured to store and eject a medicament according to a dose dialed at the drug, and wherein the second alert comprises an indication as to a correctness of the selected drug delivery device.

14. The wearable medical device of claim 1, further comprising a wireless unit configured to connect to a wireless network, wherein the memory is further configured to store a home assistant application, and wherein when the wireless unit is connected to a wireless network in a home environment, the home assistant application is executed by the processor and causes the wearable medical device to:

capture, using an optical sensor, at least one image in the home environment, identify in the at least one image objects in the home environment, determine, using the spatial sensor, distances between the objects identified in the home environment, based on the at least one image, the distances between the objects, and WiFi positioning generate a floor plan representing the home environment including the objects, and store the floor plan in the memory.

15. A computer-implemented method of using a wearable medical device the computer-implemented method comprising:

detecting, using a spatial sensor of the wearable medical device, objects in an environment, the wearable medical device comprising the spatial sensor, a processor, an acoustic signal generator, an acoustic sensor, a light source and a memory;

calculating a distance to the objects detected in the environment;

in response to determining that the distance to an object is less than a predetermined value, controlling the acoustic signal generator to generate an acoustic alert;

controlling the acoustic sensor to detect environmental acoustic signals, controlling the acoustic signal generator to generate alerts having acoustic properties that are selected based on the environmental acoustic signals detected, determining that the acoustic sensor detected environmental acoustic signals, and controlling the light source to flash and actuating or preventing the acoustic signal generator from generating the acoustic signal based on a value of the environmental acoustic signals relative to a first predetermined value and a second predetermined value.

16. The computer-implemented method of claim 15, further comprising:

generating an acoustic alert alternately on each side of the wearable medical device by activating a pair of acoustic signal generators.

17. The computer-implemented method of claim 15, further comprising:

in response to determining that the acoustic sensor detects environmental acoustic signals above the first predetermined value or below the second predetermined value, controlling the light source to flash and preventing the acoustic signal generator from generating the acoustic signal, and in response to determining that the acoustic sensor detects the environmental acoustic signals in a range between the first predetermined value and the second predetermined value, controlling the light source to flash and the acoustic signal generator to generate an alert.

18. The computer-implemented method of claim 15, further comprising:

capturing, using an optical sensor, at least one image of the environment.

19. The computer-implemented method of claim 18, further comprising:

identifying, in the at least one image, the objects in the environment; and verifying distances of the objects in the environment based on a comparison with the objects detected in the environment using the spatial sensor.

20. The computer-implemented method of claim 15, further comprising:

controlling the light source to flash relative to a respective position of the object identified in the environment of the wearable medical device.

* * * * *